US011957498B2

(12) United States Patent
Takemoto et al.

(10) Patent No.: US 11,957,498 B2
(45) Date of Patent: Apr. 16, 2024

(54) X-RAY DIAGNOSTIC APPARATUS AND MEDICAL INFORMATION PROCESSING APPARATUS

(71) Applicant: CANON MEDICAL SYSTEMS CORPORATION, Otawara (JP)

(72) Inventors: Hisato Takemoto, Nasushiobara (JP); Manabu Tanaka, Otawara (JP); Yuichiro Watanabe, Yaita (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 1011 days.

(21) Appl. No.: 16/803,559

(22) Filed: Feb. 27, 2020

(65) Prior Publication Data

US 2020/0275901 A1 Sep. 3, 2020

(30) Foreign Application Priority Data

Feb. 28, 2019 (JP) .................. 2019-035451

(51) Int. Cl.
*A61B 6/00* (2006.01)
*A61B 6/12* (2006.01)
*A61B 6/50* (2024.01)
*A61B 8/06* (2006.01)
*A61B 8/12* (2006.01)
*A61M 25/01* (2006.01)

(52) U.S. Cl.
CPC .............. *A61B 6/5217* (2013.01); *A61B 6/12* (2013.01); *A61B 6/4441* (2013.01); *A61B 6/481* (2013.01); *A61B 6/504* (2013.01); *A61B 6/507* (2013.01); *A61B 6/5247* (2013.01); *A61B 6/54* (2013.01); *A61B 8/06* (2013.01); *A61B 8/12* (2013.01); *A61M 25/0108* (2013.01)

(58) Field of Classification Search
CPC ..................................................... A61B 6/5217
See application file for complete search history.

(56) References Cited

U.S. PATENT DOCUMENTS

2014/0204124 A1* 7/2014 Auvray ................. G06T 3/0068
345/634
2018/0092608 A1* 4/2018 Schafer ................ A61B 6/5205

FOREIGN PATENT DOCUMENTS

JP 2014-525308 A 9/2014
JP 2018-46909 A 3/2018

* cited by examiner

*Primary Examiner* — Joseph M Santos Rodriguez
(74) *Attorney, Agent, or Firm* — Oblon, McClelland, Maier & Neustadt, L.L.P.

(57) ABSTRACT

In one embodiment, an X-ray diagnostic apparatus includes an X-ray source, an X-ray detector, an arm, and processing circuitry. The arm supports the X-ray source and the X-ray detector. The processing circuitry identifies a three-dimensional running direction of a blood vessel of an object from a plurality of images that are obtained by using the X-ray source and the X-ray detector to image the object from at least two different angles, and controls positions of the X-ray source and the X-ray detector by using the arm in such a manner that a target position of the blood vessel is imaged from the at least two different directions determined depending on the three-dimensional running direction.

16 Claims, 20 Drawing Sheets

X-RAY DIAGNOSTIC APPARATUS AND MEDICAL INFORMATION PROCESSING APPARATUS

CROSS-REFERENCE TO RELATED APPLICATION

This application is based upon and claims the benefit of priority from Japanese Patent Application No. 2019-035451, filed on Feb. 28, 2019, the entire contents of which are incorporated herein by reference.

FIELD

Disclosed Embodiments relate to an X-ray diagnostic apparatus and a medical information processing apparatus.

BACKGROUND

Among various X-ray diagnostic apparatuses, a known X-ray diagnostic apparatus has a configuration appropriate for imaging a circulatory system such as cerebral blood vessels, the heart, and coronary arteries. The X-ray diagnostic apparatus for imaging a circulatory system is also referred to as an X-ray angiography apparatus. In the X-ray angiography apparatus, a pair of an X-ray source and an X-ray detector are supported or held at both ends of a holding body called, for example, a C-arm. The X-ray angiography apparatus can image a region of interest of an object while arbitrarily changing the X-ray irradiation direction with respect to the region of interest by using the C-arm.

In the treatment of the circulatory system, PTCA (Percutaneous Transluminal Coronary Angioplasty) or PCI (Percutaneous Coronary Intervention) is known as treatment in which a thin tube called a catheter is inserted from an artery at, for example, the base of the foot, the wrist, or the elbow. One method of PCI is stent treatment.

In the stent treatment, a catheter, in which a metallic tubular device (i.e., stent) with a thin mesh is placed on the balloon, is guided to the stenosis of the blood vessel. Thereafter, the balloon is inflated to stretch the blood vessel from the inside, then the stent is implanted (i.e., left behind) to support the stretched vessel wall from the inside, and then the balloon is deflated and the catheter is withdrawn. The stenosis of the blood vessel is expanded by the expanded stent.

After stent treatment, it is checked whether the stent is properly placed in the blood vessel or not. For example, it is checked whether the stent is properly expanded and placed in the stenosis of the blood vessel or not.

Conventionally, in order to check the state of the implanted stent, a method of imaging around the location of the implanted stent by manually rotating and/or moving the C-arm has been used. However, it has been difficult to manually move the C-arm in a desired direction and to a desired position in order to obtain a desired image for checking.

Additionally, it is conceivable to check the state of the implanted stent by using an intravascular ultrasonic imaging device such as IVUS (Intervascular Ultrasound) for imaging the treated region from the inside of the stent placed in the blood vessel. However, the examination using IVUS imposes a further burden on the patient and its examination time becomes longer.

For this reason, there is a demand for an X-ray diagnostic apparatus that can readily and reliably check a result of PCI treatment such as the state of the implanted stent.

DETAILED DESCRIPTION

First Embodiment

A description of embodiments will now be given by referring to the accompanying drawings. In the following embodiments, respective components assigned with the same reference sign are assumed to operate and function in the same manner, and duplicate description is omitted.

In one embodiment, an X-ray diagnostic apparatus includes an X-ray source, an X-ray detector, an arm, and processing circuitry. The arm supports the X-ray source and the X-ray detector. The processing circuitry identifies a three-dimensional running direction of a blood vessel of an object from a plurality of images that are obtained by using the X-ray source and the X-ray detector to image the object from at least two different angles, and controls positions of the X-ray source and the X-ray detector by using the arm in such a manner that a target position of the blood vessel is imaged from the at least two different directions determined depending on the three-dimensional running direction.

Figure 1:
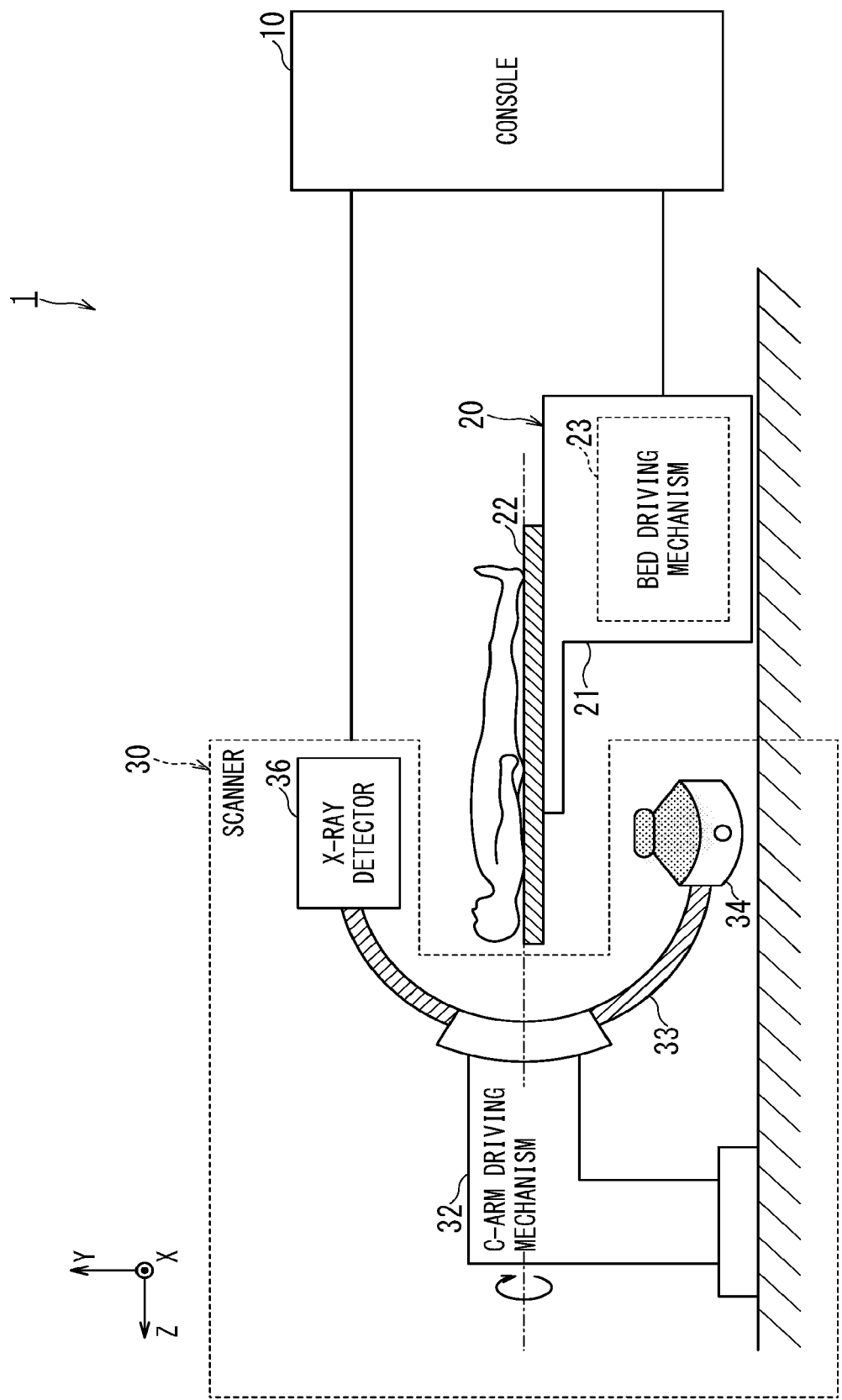
FIG. 1 is a configuration diagram illustrating the overall configuration of an X-ray diagnostic apparatus according to the first embodiment.

FIG. 1 is a block diagram illustrating the overall configuration of the X-ray diagnostic apparatus 1 according to the first embodiment. The X-ray diagnostic apparatus 1 includes a console 10, a bed 20, and a scanner 30.

The scanner 30 includes an X-ray source 34, an X-ray detector 36, a C-arm 33, and a C-arm driving mechanism 32. The C-arm 33 supports the X-ray source 34 at its one end and supports the X-ray detector 36 at the opposite end such that the X-ray source 34 and the X-ray detector 36 are disposed to face each other with an object interposed therebetween.

The C-arm 33 is supported by the C-arm driving mechanism 32. The C-arm driving mechanism 32 integrally moves the X-ray source 34 and the X-ray detector 36 in an arc along the arc direction of the C-arm 33 under the control of the console 10. Further, under the control of the console 10, the C-arm driving mechanism 32 can rotate the C-arm 33 around the rotation axis indicated by the chain line in FIG. 1 so as to integrally rotate the X-ray source 34 and the X-ray detector 36 around the object.

The midpoint of the line connecting the X-ray source 34 to the X-ray detector 36 is defined as an isocenter. Then, under the control of the console 10, the X-ray source 34 and the X-ray detector 36 can rotate along a circular orbit on a plane of arbitrary inclination passing through this isocenter.

The X-ray source 34 includes: an X-ray tube that receives high-voltage power and radiates X-rays toward an object; an X-ray field diaphragm composed of lead blades; and a compensation filter that is made of, for example, silicon rubber and attenuates a predetermined amount of radiated X-rays for preventing halation.

The X-ray detector 36 includes a flat panel detector (FPD), detects X-rays having passed through the object and converts them into electric signals by using detection elements arrayed on a two-dimensional plane. The X-ray detector 36 may be configured as a detector provided with an I. I. (Image Intensifier) and a TV instead of the FPD. The X-ray detector 36 further converts the analog electric signals, which are converted from the X-rays, into digital signals and outputs the digital signals to the console 10.

The bed 20 includes: a table 22 on which the object is placed; a table supporter 21 that supports the table 22; and a bed driving mechanism 23 that drives the table 22 in the horizontal direction and in vertical direction on the basis of instructions from the console 10.

The console 10 controls the scanner 30 and the bed 20, and generates X-ray radiographic images (i.e., still images) and X-ray fluoroscopic images (i.e., live images) on the basis of the signals outputted from the X-ray detector 36.

Figure 2:
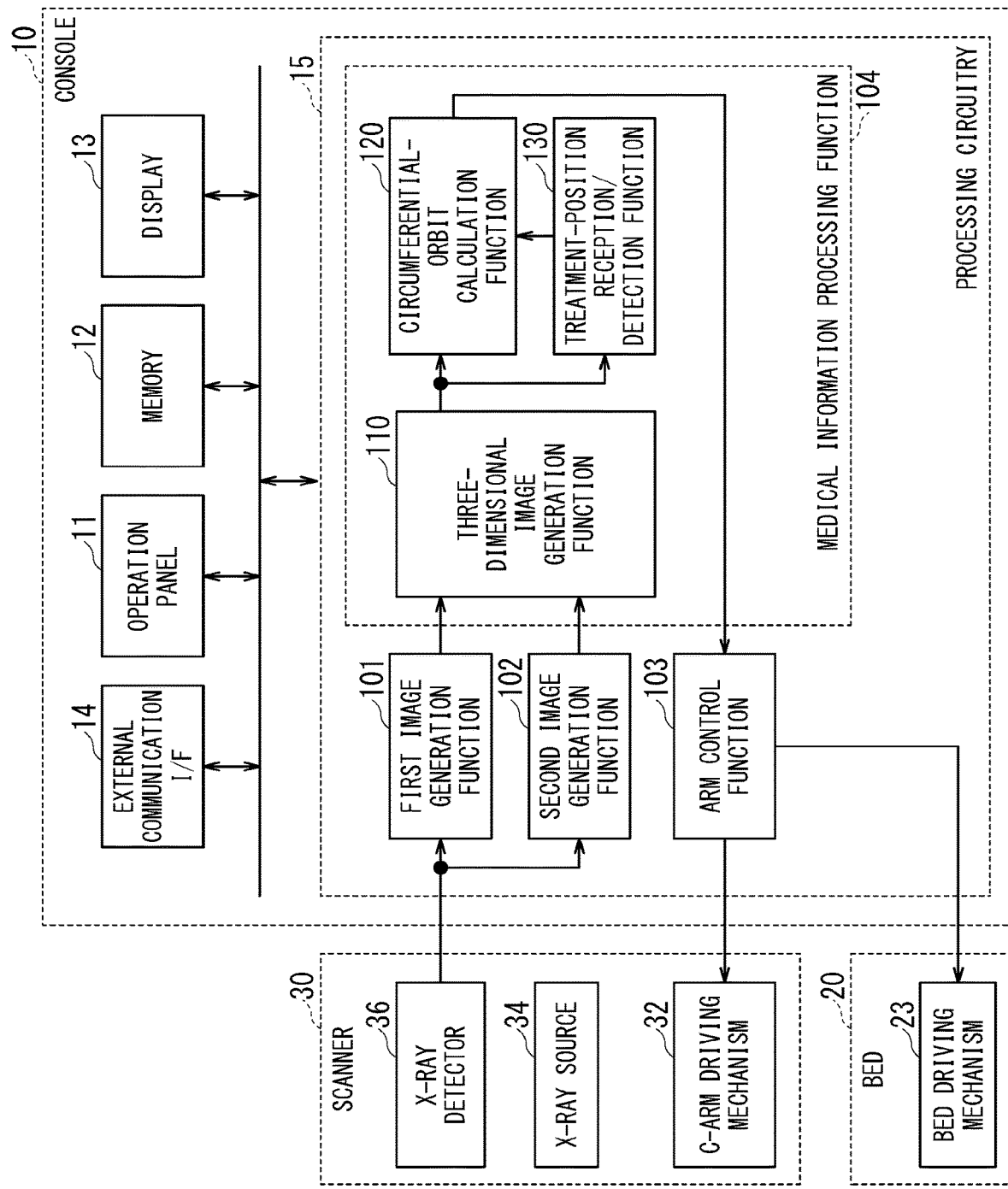
FIG. 2 is a block diagram illustrating a configuration and functions of a console according to the first embodiment.

FIG. 2 is a block diagram illustrating the detailed configuration and the functions of the console 10. As shown in FIG. 2, the console 10 includes: an operation panel 11; a memory 12; a display 13; an external communication I/F 14; and processing circuitry 15.

The operation panel 11 includes input devices for inputting various information and data such as various imaging conditions of the scanner 30 and driving conditions of the C-arm 33 and the bed 20. The input devices are various types of devices such as a joystick, a trackball, a switch, a button, a mouse, a keyboard, a numeric keypad, and a touch panel for inputting various information and data.

The display 13 is configured as a general display device such as a liquid crystal display or an OLED (Organic Light Emitting Diode) display, and displays various information and various data in addition to images such as X-ray fluoroscopic images and X-ray radiographic images.

The external communication I/F 14 connects the X-ray diagnostic apparatus 1 to other devices according to various communication protocols. For this connection, various communication networks can be used such as a wireless/wired in-hospital local area network (LAN), the Internet network, a telephone communication line network, an optical fiber communication network, and a cable communication network.

The memory 12 has a configuration including a recording medium readable by a processor, such as a semiconductor memory and a magnetic or optical recording medium. The memory 12 stores various software programs to be executed by the processor in addition to data related to images and various imaging conditions.

The processing circuitry 15 is, for example, a circuit provided with a CPU (Central Processing Unit) and/or a special-purpose or general-purpose processor. The processor implements various functions described below by executing the programs stored in the memory 12. The processing circuitry 15 may be configured of hardware such as a field programmable gate array (FPGA) and an application specific integrated circuit (ASIC). The various functions described below can also be implemented by such hardware. Additionally, the processing circuitry 15 can implement the various functions by combining hardware processing and software processing based on its processor and programs.

Further, the processing circuitry 15 may be configured by combining a plurality of independent processors so that the respective processors implement the corresponding functions. When a plurality of processors are provided, the memory for storing the programs may be provided for each processor individually or a single memory may collectively store the programs corresponding to the functions of all the processors.

Next, a description will be given of the functions to be implemented by the processing circuitry 15. As shown in FIG. 2, the processing circuitry 15 implements a first image generation function 101, a second image generation function 102, an arm control function 103, and a medical information processing function 104. The medical information processing function 104 further includes a three-dimensional image generation function 110, a circumferential-orbit calculation function 120, and a treatment-position reception/detection function 130.

The first image generation function 101 generates, as a first image, a coronary angiographic image obtained by injecting a contrast medium into a blood vessel, for example, into the coronary artery of the object. The first image is generated under the condition that the C-arm 33 is set to the first angle with respect to the object.

The second image generation function 102 generates, as a second image, a device image obtained by inserting a device attached to a catheter into a blood vessel, for example, into the coronary artery of the object. The second image is generated under the condition that the C-arm 33 is set to the second angle different from the first angle, for example, by 30 degrees or more.

The three-dimensional image generation function 110 generates a three-dimensional image from at least two images including the first image and the second image that are imaged at different angles. The three-dimensional image generation function 110 uses the generated three-dimensional image for identifying the blood vessel into which the device is inserted (for example, the coronary artery into which the device is inserted), and further identifies the running direction of the identified coronary artery.

The treatment-position reception/detection function 130 receives a treatment position specified (or designated) for the three-dimensional image. Additionally or alternatively, the treatment-position reception/detection function 130 may automatically detect the treatment position from the three-dimensional image.

The circumferential-orbit calculation function 120 calculates the circumferential orbit (or trajectory) around the treatment position in the blood vessel on the basis of the running direction of the blood vessel.

The arm control function 103 rotates the pair of the X-ray source 34 and the X-ray detector 36 by rotating the C-arm 33 such that the area around the treatment position is imaged along the calculated circumferential orbit.

Figure 3:
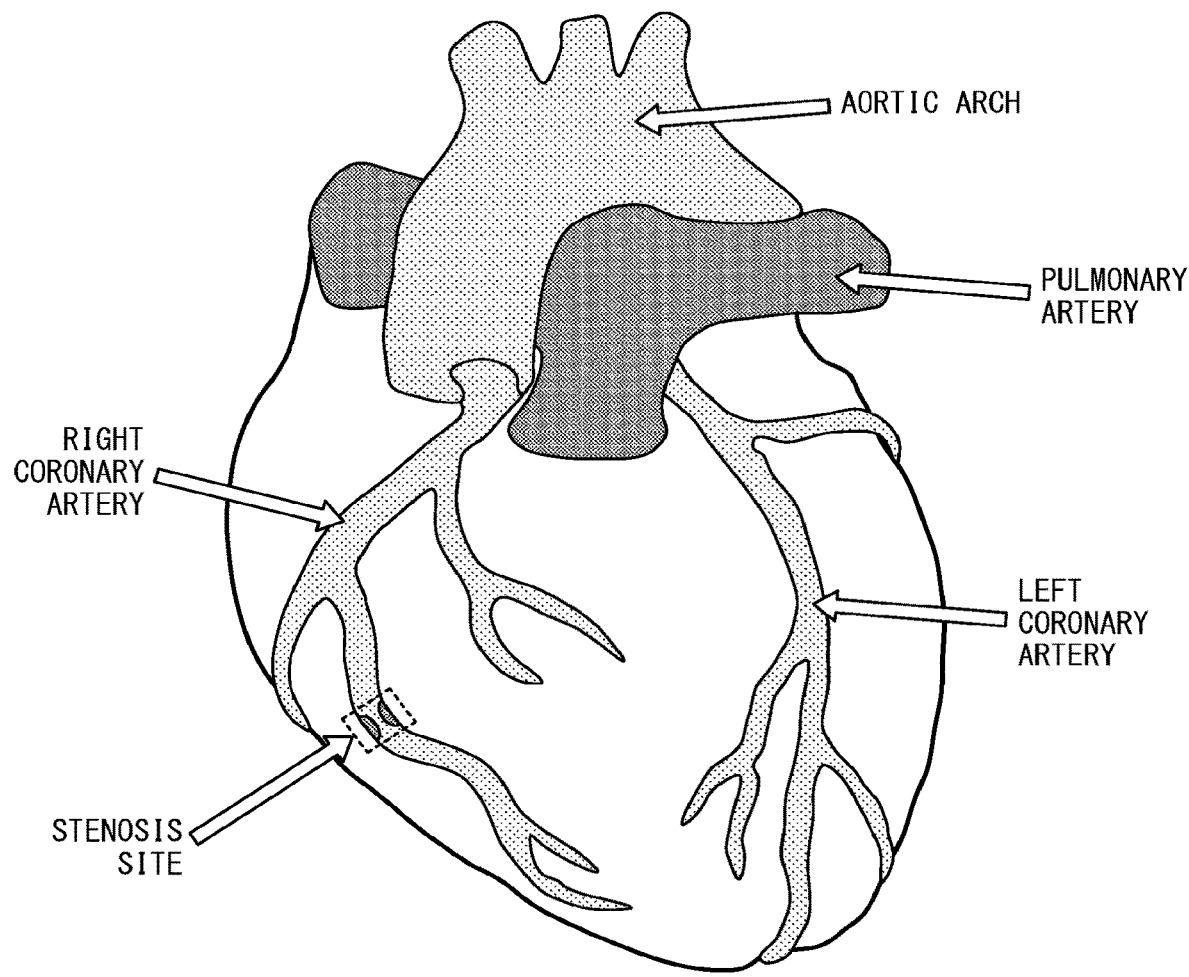
FIG. 3 is a schematic diagram illustrating a treatment position that is an imaging target of the X-ray diagnostic apparatus according to each embodiment.

FIG. 3 is a schematic diagram illustrating a treatment position that is an imaging target of the X-ray diagnostic apparatus 1 according to the embodiments described below.

As shown in FIG. 3, coronary arteries such as the right coronary artery and the left coronary artery surround the heart. Deposit such as cholesterol (fat), which is gradually deposited on the inner wall of the coronary arteries surrounding the heart, narrows the lumen of each of those blood vessels and reduce the blood flow. If the volume of blood flowing into those blood vessels is reduced because the lumen is narrowed to such an extent that sufficient oxygen and nutrients cannot be supplied to the myocardium, symptoms such as chest pain and chest tightness are caused. This is a common angina symptom. If the coronary artery is completely occluded suddenly and blood flow is interrupted, acute myocardial infarction is caused.

Catheterization or catheterization study is known as one of the examinations for coronary artery disease. In the catheterization study, a thin tube called a catheter is inserted from the blood vessel of the wrist, the arm, or the base of the foot, and then contrast-enhanced imaging is performed on the coronary artery. The catheterization study can accurately diagnose the position of the coronary artery lesion and the degree of stenosis. In the case of acute vascular disease such as acute myocardial infarction, catheter treatment is performed subsequent to the catheterization study.

Figure 4:
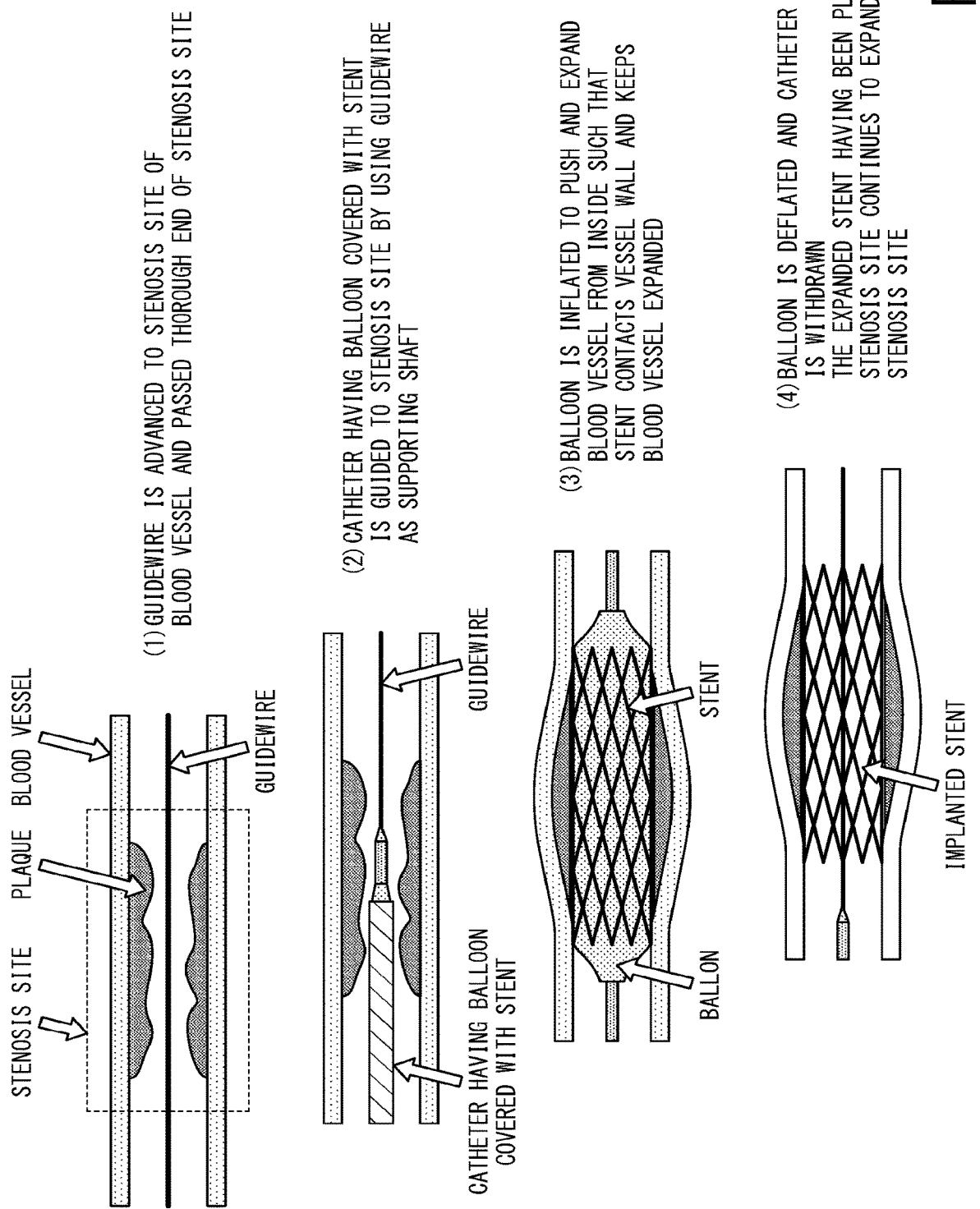
FIG. 4 is a schematic diagram illustrating a procedure of catheter treatment.

FIG. 4 is a schematic diagram illustrating a procedure of the catheter treatment. In the catheter treatment, as shown in the top stage of FIG. 4, a guidewire is advanced to the stenosis site of the blood vessel and is passed through the end of the stenosis site. Next, as shown in the second stage of FIG. 4, a catheter having a balloon covered with a stent is guided to the stenosis site by using the guidewire as a supporting shaft. Next, as shown in the third stage of FIG. 4, the balloon is inflated to push and expand the stenosis site of the blood vessel from the inside such that the stent contacts the vessel wall from the inside. Finally, as shown in the bottom stage of FIG. 4, the balloon is deflated and the catheter is withdrawn. The expanded stent having been placed in the stenosis site continues to expand the stenosis site of the blood vessel.

After the stent treatment, it is checked whether the stent is properly placed in the blood vessel or not. For example, it is checked whether the stent is properly expanded and placed in the stenosis site of the blood vessel or not.

In the conventionally method for checking the state of the implanted stent, the periphery of the position of the implanted stent is imaged by manually rotating and moving the C-arm. However, it has been difficult to manually move the C-arm to a desired position and in a desired direction for obtaining a desired image for the checking.

To solve the above-described problem, the X-ray diagnostic apparatus 1 according to the present embodiment achieves a function of readily and reliably checking the state of the implanted stent.

Figure 5:
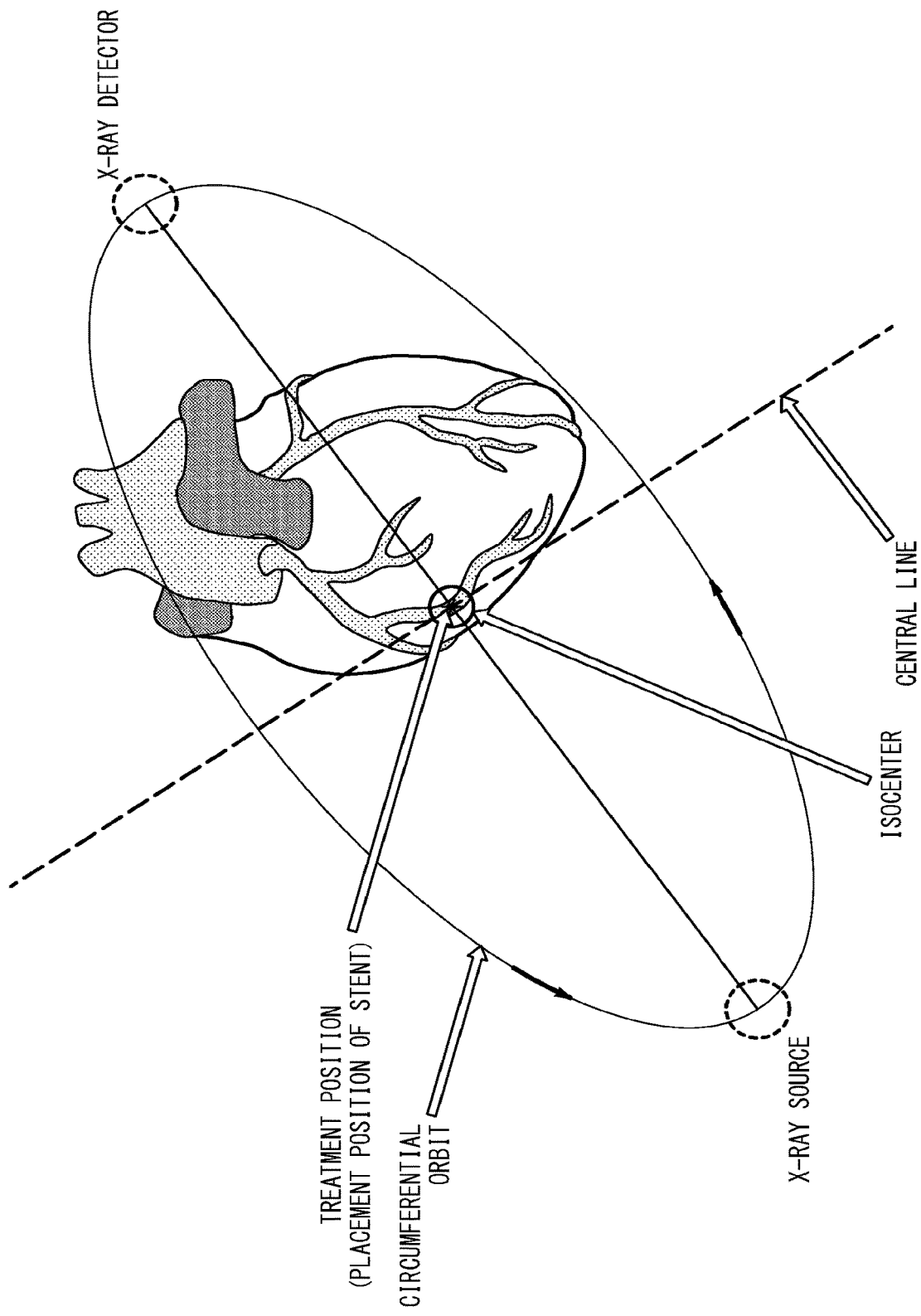
FIG. 5 is a schematic diagram illustrating a concept of functions to be implemented by the X-ray diagnostic apparatus according to each embodiment.

FIG. 5 is a schematic diagram illustrating a concept of functions to be implemented by the X-ray diagnostic apparatus 1.

As shown in FIG. 5, when an input for specifying the treatment position of the coronary artery is received or when the treatment position is detected, the X-ray diagnostic apparatus 1 according to the present embodiment calculate a circumferential orbit centering on the treatment position within the plane that is perpendicular to the running direction of the blood vessel and includes the treatment position. The treatment position is the position of the implanted stent or the position where the stent is to be implanted.

By rotating the pair of the X-ray source 34 and the X-ray detector 36 on the calculated circumferential trajectory by the C-arm 33, the condition of the implanted stent can be observed along the circumferential trajectory in a plane orthogonal to the blood vessel. During this observation period, the position of the implanted stent and the isocenter (that is, the center of the line connecting the X-ray source 34 and the X-ray detector 36) are kept to be coincident with each other.

Figure 6:
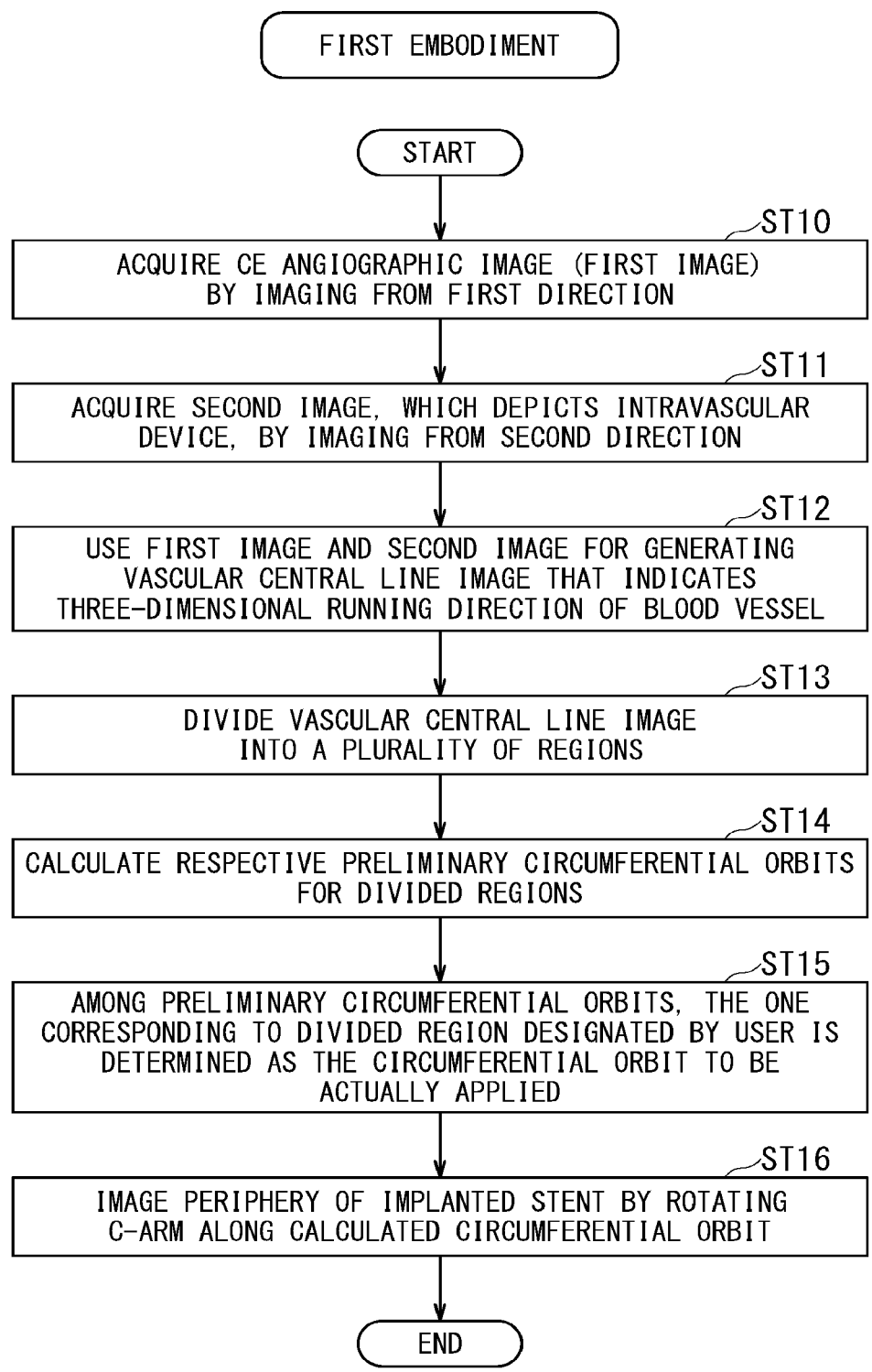
FIG. 6 is a flowchart illustrating an operation to be executed by the X-ray diagnostic apparatus according to the first embodiment.
Figure 7:
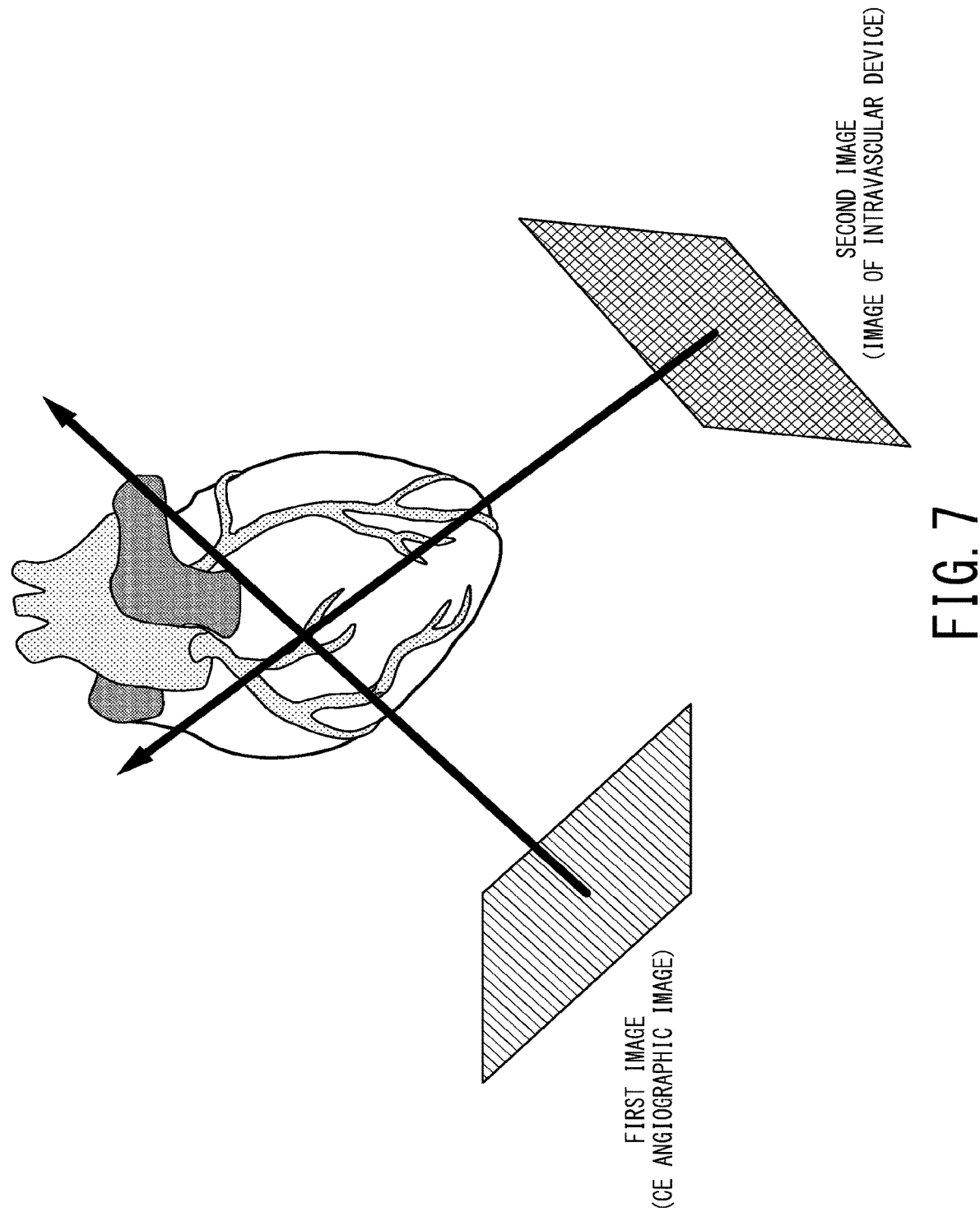
FIG. 7 is a first schematic diagram illustrating an operation concept of the X-ray diagnostic apparatus according to the first embodiment.
Figure 8:
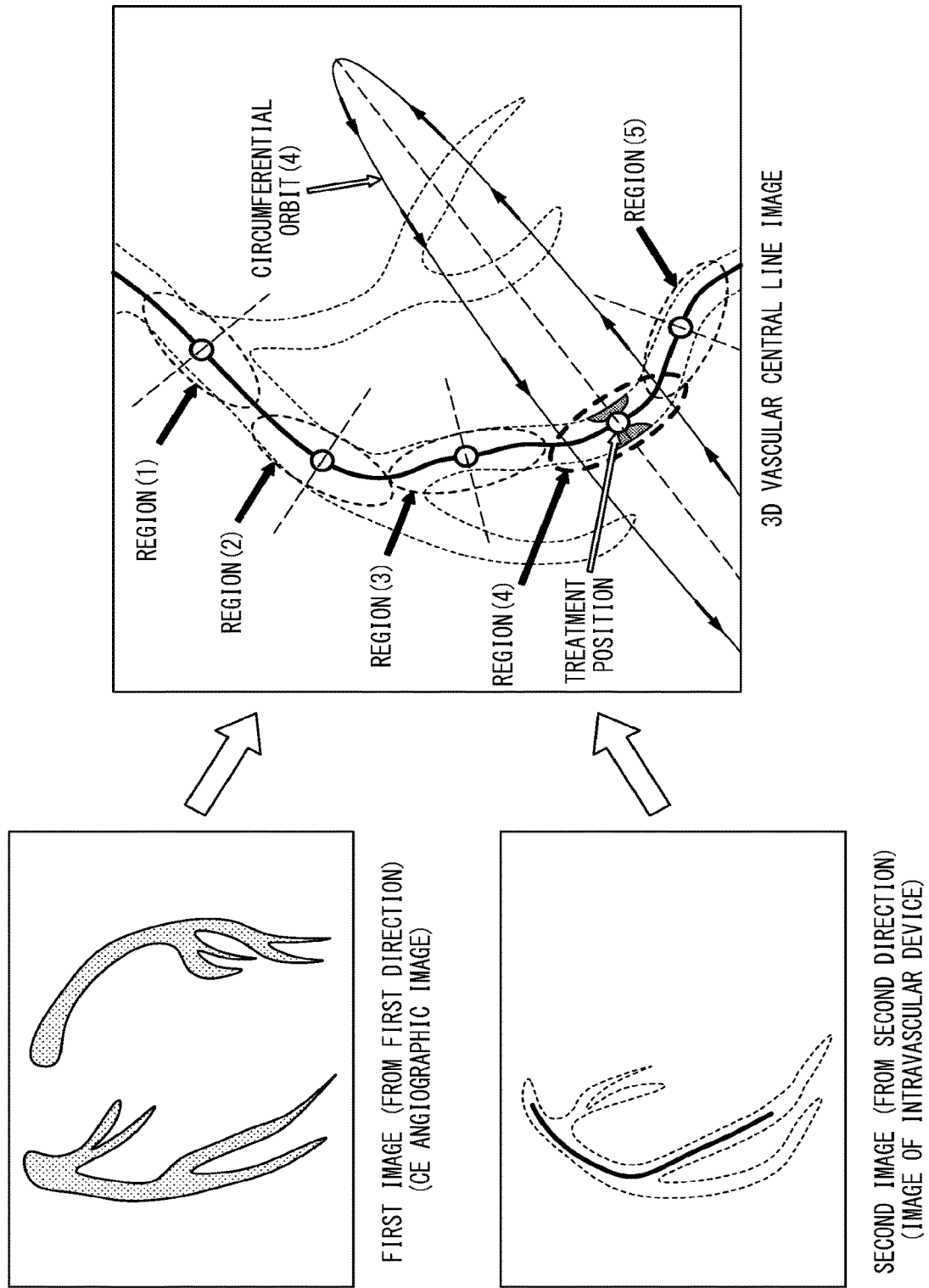
FIG. 8 is a second schematic diagram illustrating the operation concept of the X-ray diagnostic apparatus according to the first embodiment.

FIG. 6 is a flowchart illustrating an operation to be executed by the X-ray diagnostic apparatus 1 according to the first embodiment. FIG. 7 and FIG. 8 are schematic diagrams illustrating the operation concept of the X-ray diagnostic apparatus 1 according to the first embodiment. Prior to the stent treatment, usually, coronary angiographic images are acquired after an injection of the contrast agent. Thus, in the step ST10 of FIG. 6, a contrast enhanced (CE) angiographic image (for example, a CE coronary angiographic image) from the first direction is acquired as the first image, as shown in the left part of FIG. 7 and the upper left part of FIG. 8.

In the step ST11, an image, which depicts the intravascular treatment instrument and has been imaged from the second direction, is acquired as the second image, as shown in the right part of FIG. 7 and the lower left part of FIG. 8. The second direction needs to be separated by a predetermined angle or more with respect to the first direction. For example, it is preferred that the second direction is separated by 30 degrees or more with respect to the first direction.

The intravascular treatment instrument to be imaged as the second image in the first embodiment is not particularly limited to a specific type. As long as the intravascular treatment instrument is a catheter that reaches the treatment position (i.e., the stenosis site where the stent is to be placed), the type of device at the tip of the catheter is not limited to a specific one. For example, the device to be attached to the tip of the catheter may be an intravascular ultrasound (IVUS) imaging device for inspecting a stenosis before the stent treatment, may be a balloon associated with the stent treatment, or may be a stent in itself.

In imaging with the use of an intravascular treatment instrument, in general, a contrast agent is not used. Thus, as illustrated by the thick solid line in the lower left part of FIG. 8, in the second image, the guidewire inserted into the core of the catheter is mainly depicted.

The processing of the step ST10 is achieved by the first image generation function 101 shown in FIG. 2, and the processing of the step ST11 is achieved by the second image generation function 102.

The right part of FIG. 8 illustrates the concept of processing from the steps ST12 to ST15 in FIG. 6.

In the step ST12, a vascular central line image indicating the three-dimensional running direction of the blood vessel is generated from the first image and the second image. A three-dimensional vascular central line image may be generated from three or more images that have been imaged from three or more directions.

A known technique can be applied to the method of generating a three-dimensional image from respective two-dimensional images that are imaged from two or more different directions. For example, segmentation is performed on the first image and the second image, which are two-dimensional images, to extract a blood vessel region and a guidewire region, and then epipolar geometry is used to generate a three-dimensional vascular central line image of the blood vessel in which the device is inserted (i.e., the blood vessel to be treated). The three-dimensional vascular central line image does not need to provide information on the exact shape of the blood vessel as long as it can provide the running direction of the blood vessel (i.e., central line of the blood vessel). The processing of the step ST12 is achieved by the three-dimensional image generation function 110 shown in FIG. 2.

In the next step ST13, the vascular central line image is divided into a plurality of regions. For example, as shown in the right part of FIG. 8, the image is divided into a plurality of regions such as the region (1), the region (2), the region (3), the region (4), and the region (5).

In the next step ST14, a preliminary circumferential orbit is calculated for each of the divided regions. The preliminary circumferential orbit is a circular orbit on the plane that includes the midpoint of the central line of the divided region and is orthogonal to the central line. In other words, the center of the preliminary circumferential orbit is the midpoint of the central line, and the diameter of the preliminary circumferential orbit is, for example, the distance between the X-ray source 34 and the X-ray detector 36. The processing of the steps ST13 and ST14 is achieved by the circumferential-orbit calculation function 120 shown in FIG. 2.

The schematic diagram illustrating the preliminary circumferential orbits of the respective divided regions is displayed on the display 13 of the console 10 as in the right part of FIG. 8, for example. A user selects a desired one from the plurality of the divided regions displayed on the display 13.

In the next step ST15, selection of one divided region by the user is accepted. Among a plurality of the preliminary circumferential orbits, which have the same number of the preliminary circumferential orbits as the divided regions, the preliminary circumferential orbit of the divided region selected by the user is determined as the circumferential orbit to be actually applied. The processing of the step ST15 is achieved by the treatment-position reception/detection function 130 shown in FIG. 2.

In the next step ST16, the C-arm 33 is rotated along the determined circumferential orbit, and the periphery of the implanted stent is imaged from a plurality of locations. The processing of the step ST16 is achieved by the arm control function 103 shown in FIG. 2.

According to the first embodiment described above, the X-ray diagnostic apparatus 1 can readily image the periphery of the implanted stent from a plurality of positions on the circumferential orbit having its center at the position of the implanted stent and in directions orthogonal to the central line of the blood vessel around the implanted stent. Thus, a user can readily and reliably check the condition of the implanted stent from the images which are imaged in the above-described manner.

SECOND EMBODIMENT

Figure 9:
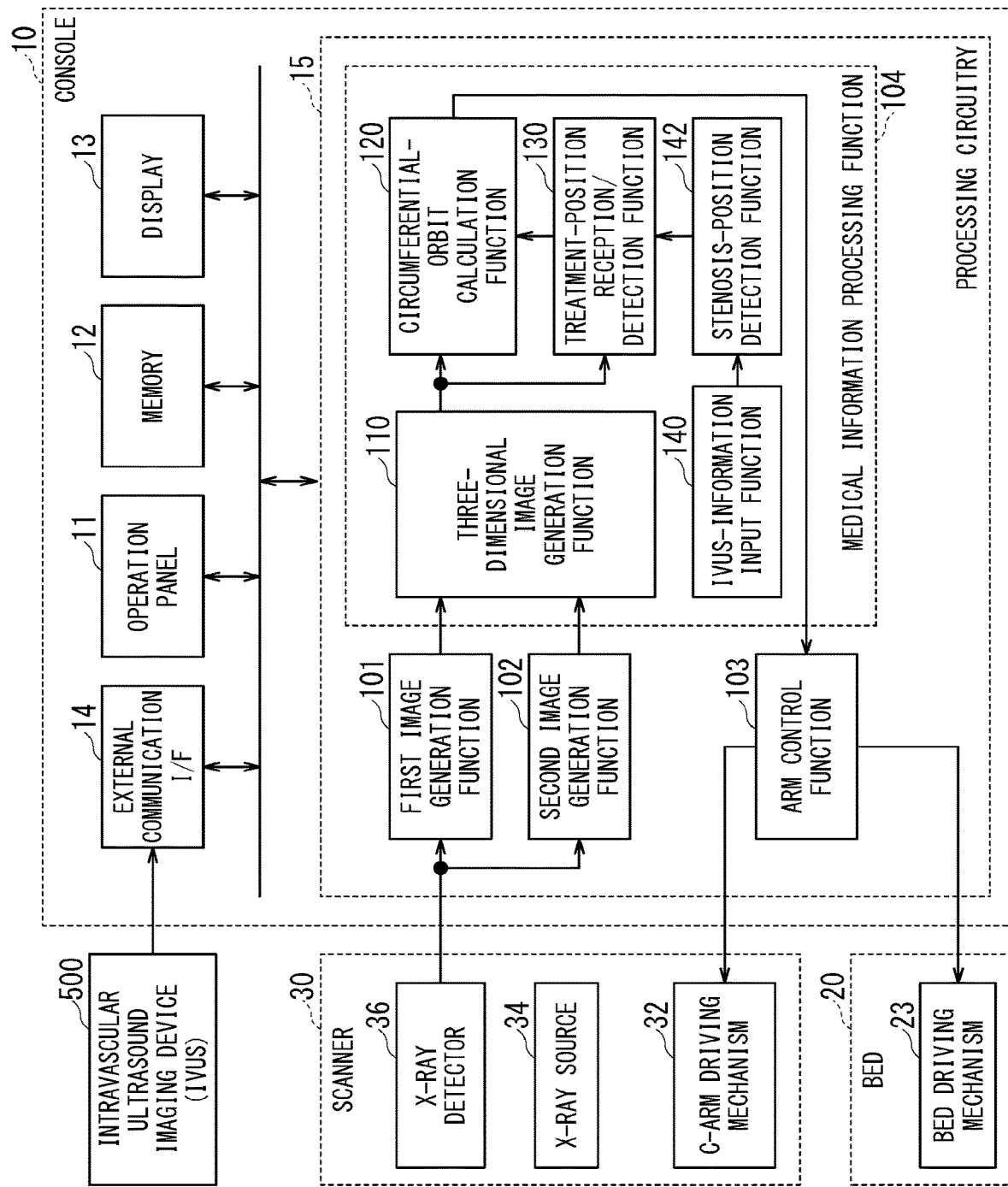
FIG. 9 is a block diagram illustrating a configuration and functions of the console according to the second embodiment.
Figure 10:
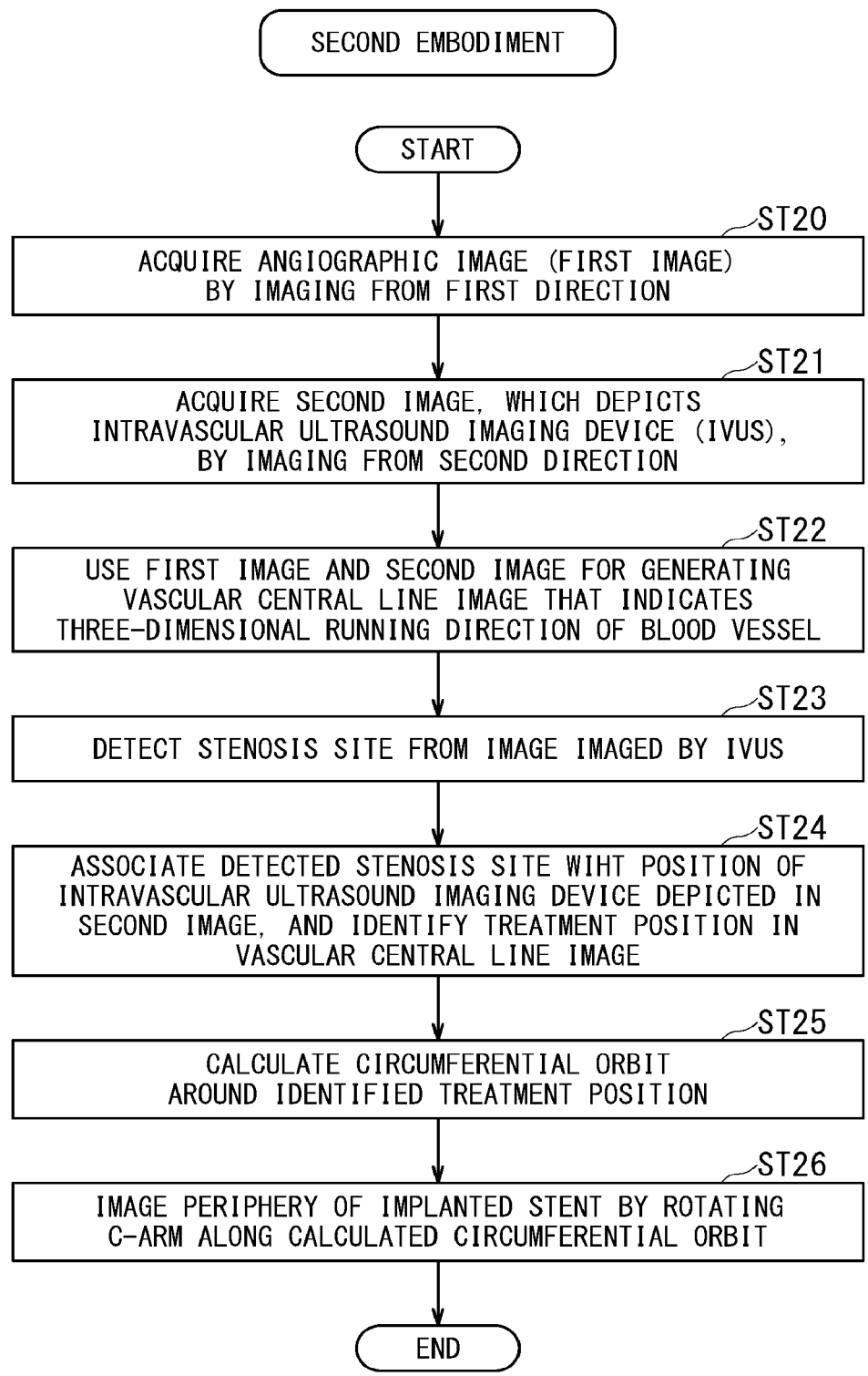
FIG. 10 is a flowchart illustrating an operation to be executed by the X-ray diagnostic apparatus according to the second embodiment.
Figure 11:
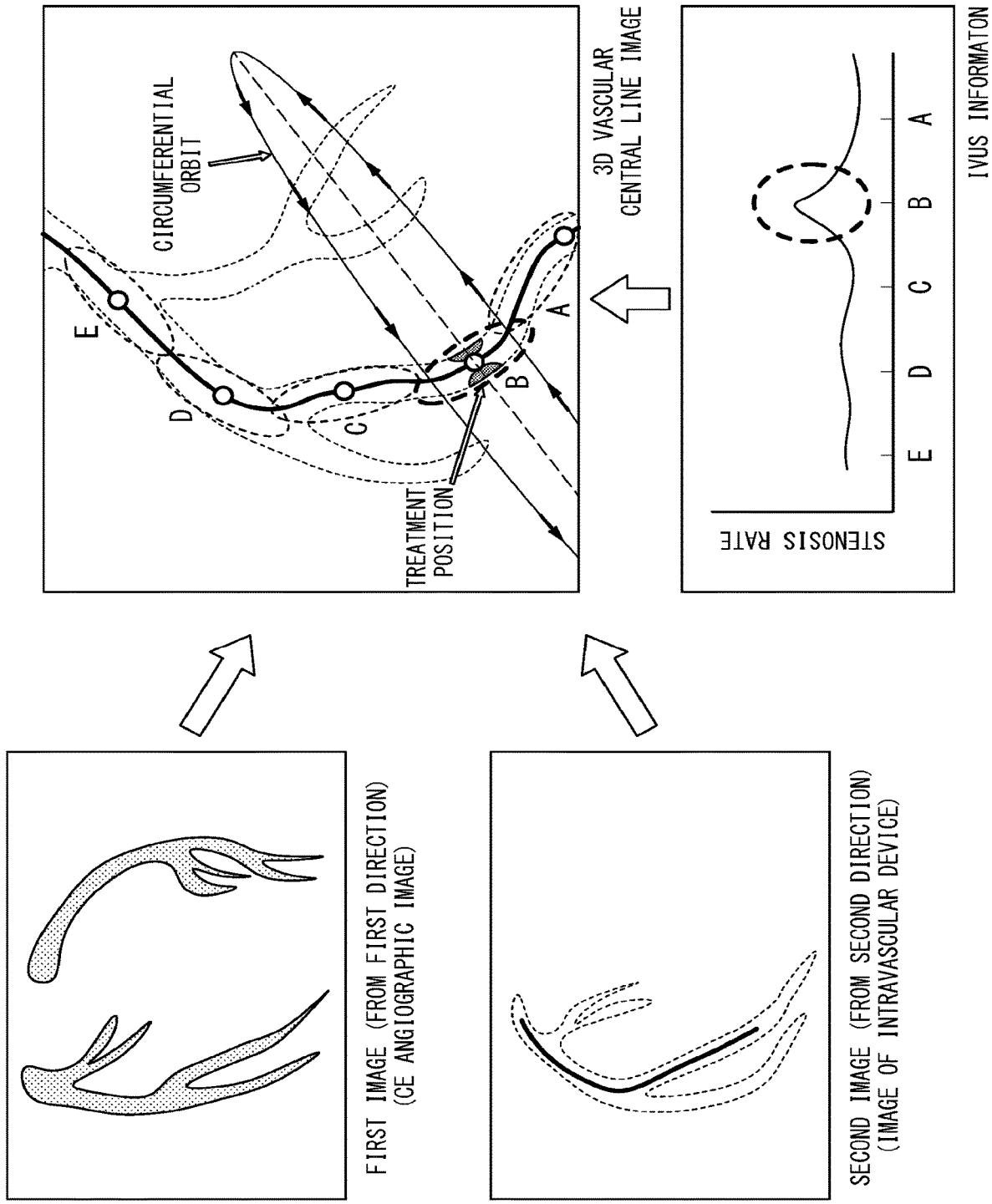
FIG. 11 is a schematic diagram illustrating an operation concept of the X-ray diagnostic apparatus according to the second embodiment.

FIG. 9 is a block diagram illustrating a detailed configuration and functions of the X-ray diagnostic apparatus 1 according to the second embodiment. FIG. 10 is a flowchart illustrating an operation to be executed by the X-ray diagnostic apparatus 1 according to the second embodiment. FIG. 11 is a schematic diagram illustrating an operation concept of the X-ray diagnostic apparatus 1 according to the second embodiment.

The X-ray diagnostic apparatus 1 of the second embodiment differs from the first embodiment in at least the following two points. The first difference is the type of intravascular device to be used. Although the intravascular device to be used is not limited in the first embodiment, the second embodiment adopts a device that can acquire information related to stenosis of the blood vessel, such as an intravascular ultrasound (IVUS) imaging device. For example, an intravascular ultrasound (IVUS) imaging device can provide tomographic images of a blood vessel in real time by using an ultrasound transducer attached to the tip of the catheter. On the basis of the tomographic images of the blood vessel, the state of the stenosis and a stenosis index such as a stenosis rate can be obtained.

The second difference is that the configuration of the second embodiment has a function of associating the stenosis-related index obtained by the intravascular ultrasonic imaging device with the position in the blood vessel where the index is obtained. This function is also called Co-Registration. When imaging is performed while the intravascular ultrasound imaging device is being pulled back from a predetermined position in the blood vessel, for example, the start position and the end position of the pullback are associated with each other in the image (i.e., second image) generated by the intravascular ultrasound imaging device, and the position of the ultrasound transducer during the pullback motion is associated with the ultrasonic image generated by the intravascular ultrasound imaging device. Consequently, as denoted by "A", "B", "C", "D", and "E" in the upper right part and the lower right part of FIG. 11, the position of the blood vessel, in which the intravascular ultrasound imaging device has been inserted, can be associated with a hemadostenosis-related index value such as a stenosis rate obtained from the ultrasound image. From such association, it can be estimated that the position having the highest stenosis rate is the position where the stent is to be placed (i.e., the treatment position).

In the block diagram of FIG. 9, the above-described function is implemented by an IVUS-information input function 140 and a stenosis-position detection function 142. The IVUS-information input function 140 inputs stenosis-related information including intravascular ultrasound images and the index value such as a stenosis rate from the intravascular ultrasound imaging device 500 shown in FIG. 9 into the stenosis-position detection function 142 via the external communication I/F 14. The stenosis-position detection function 142 associates the index value such as a stenosis rate with the position of the blood vessel in which the device has been inserted (for example, regions A, B, C, D, E in FIG. 11), and causes the display 13 to display a diagram as illustrated in the upper right part of FIG. 11, for example.

The treatment-position reception/detection function 130 may receive designation from the user who views the display 13, for example, designation that the region B is the treatment position. Additionally or alternatively, on the basis of the result of the association by the stenosis-position detection function 142, the treatment-position reception/detection function 130 may automatically detect that the region B is the treatment position.

The circumferential-orbit calculation function 120 calculates the circumferential orbit around the region B designated by the user or the region B automatically detected by the apparatus in a manner similar to the first embodiment.

In the flowchart of FIG. 10, the processing of the steps ST23 and ST24 corresponds to the above-described functions of the second embodiment. The processing of the steps ST20, ST21, ST22, ST25, and ST26 is the same as that of the first embodiment.

As the intravascular device of the second embodiment, an intravascular device in which a pressure transducer is attached to the tip of the catheter can be used instead of the intravascular ultrasonic imaging device. When the pressure in the blood vessel is measured by using the pressure transducer, a hemadostenosis-related index such as FFR (Fractional Flow Reserve) and IFR (Instantaneous wave-Free Ratio) can be obtained.

According to the second embodiment, the X-ray diagnostic apparatus 1 can accurately provide a user with the stenosis position in the blood vessel (i.e., the treatment position) on the basis of an ultrasonic image obtained by an intravascular ultrasonic imaging device and a hemadostenosis-related index such as FFR and IFR. Instead of accepting designation of the position from the user, the apparatus can automatically detect the treatment position.

THIRD EMBODIMENT

Figure 12:
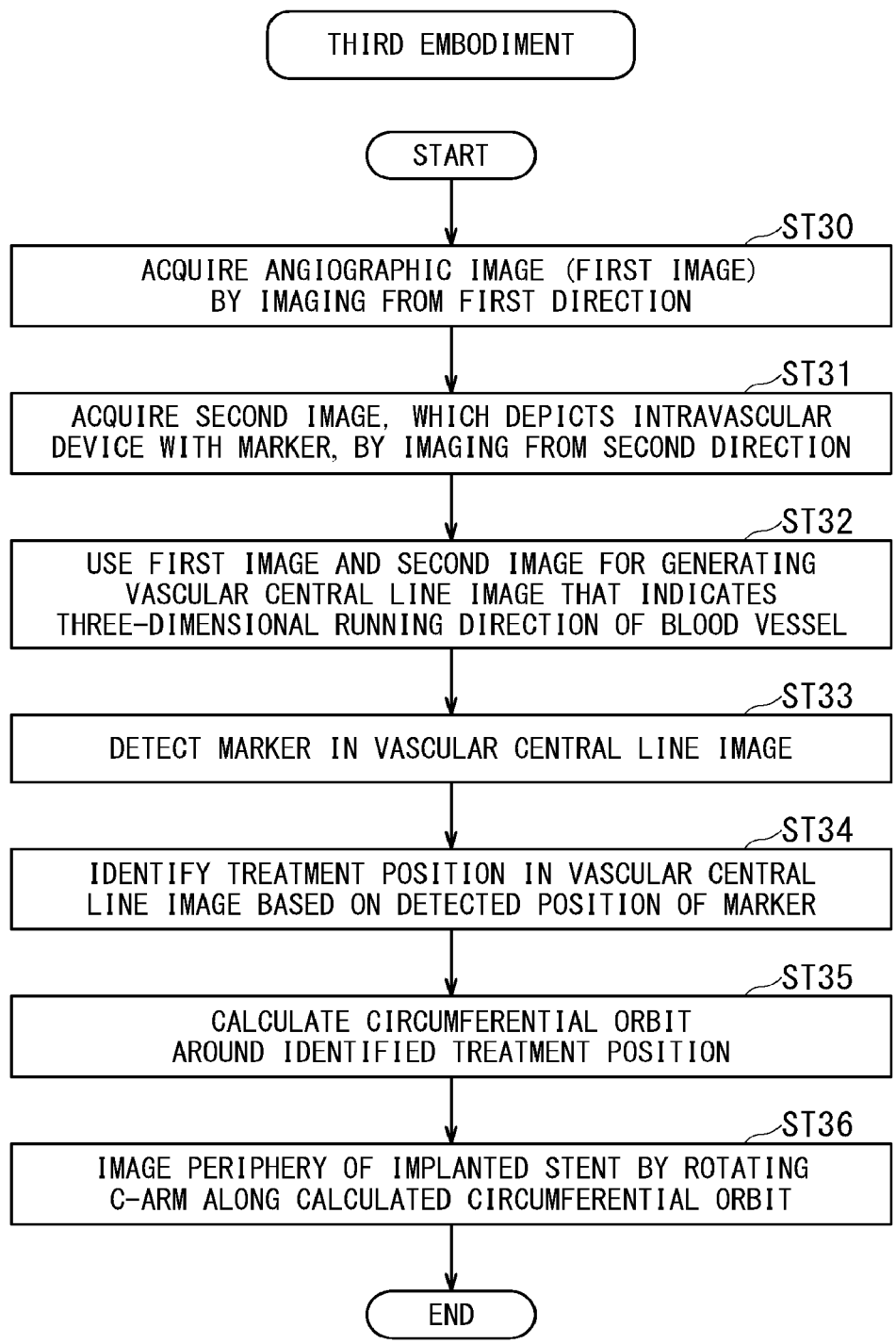
FIG. 12 is a flowchart illustrating an operation to be executed by the X-ray diagnostic apparatus according to the third embodiment.
Figure 13:
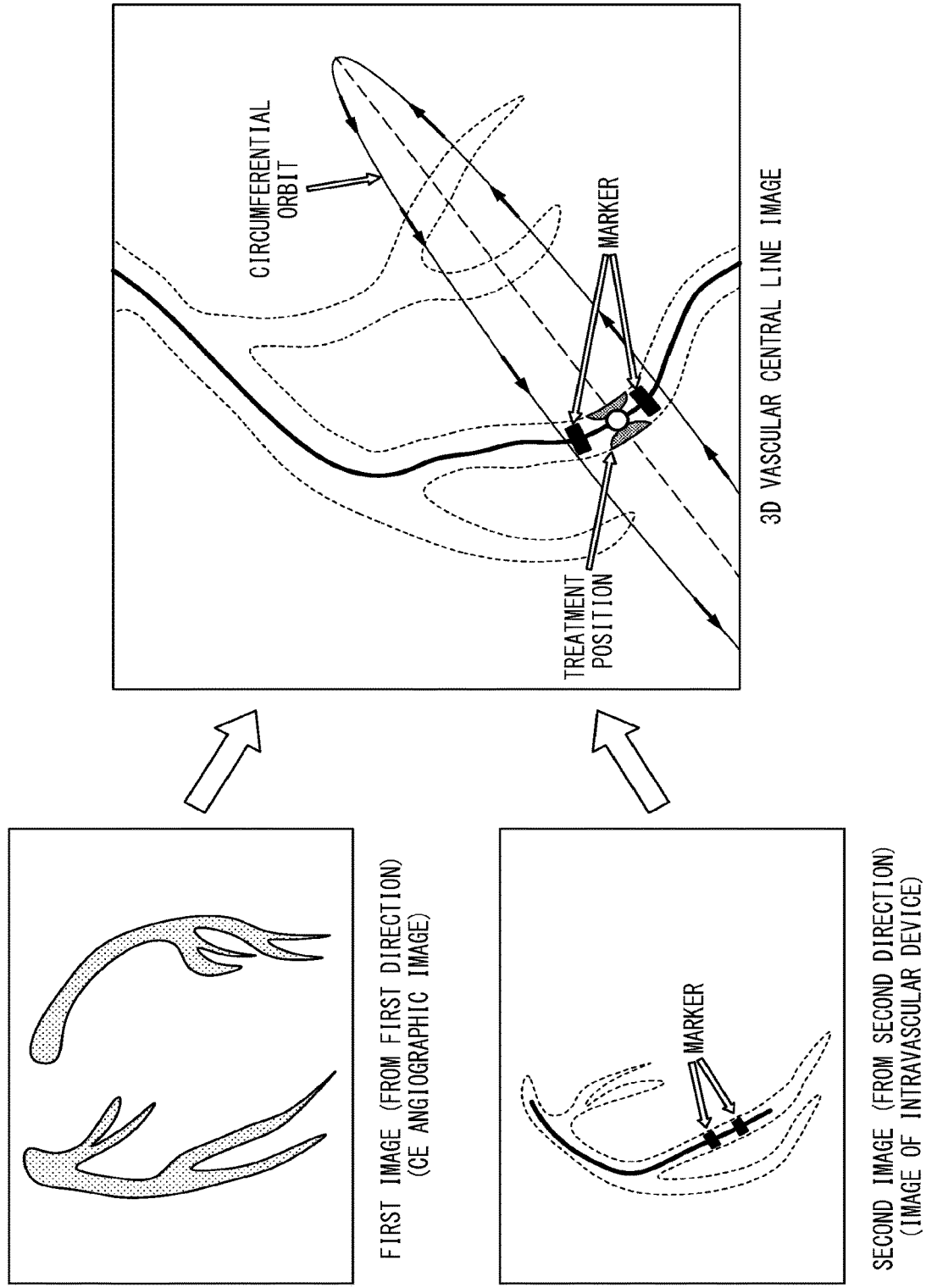
FIG. 13 is a schematic diagram illustrating an operation concept of the X-ray diagnostic apparatus according to the third embodiment.

FIG. 12 is a flowchart illustrating an operation to be executed by the X-ray diagnostic apparatus 1 according to the third embodiment. FIG. 13 is a schematic diagram illustrating an operation concept of the X-ray diagnostic apparatus 1 according to the third embodiment.

The X-ray diagnostic apparatus 1 of the third embodiment differs from the first embodiment in that the second image is acquired by using an intravascular device with a marker. The intravascular device with a marker is, for example, a device in which a radiopaque substance (i.e., marker) is provided at the position(s) corresponding to at least one of the front end and the rear end of the balloon or the stent.

In the second image obtained by imaging the intravascular device without a marker, the guidewire can be detected but the respective portions of the balloon and the stent are not necessarily depicted satisfactorily. In the second image obtained by imaging the intravascular device with a marker, the marker is satisfactorily depicted and thus the position of the balloon and/or the stent can be visually checked readily or be automatically detected by the apparatus. The position where the marker is stopped for a predetermined time or more may be considered to be the position where the stent is placed. In other words, it can be estimated that the position where the marker has stopped for a predetermined time or more is the treatment position.

Accordingly, in the third embodiment, as shown in the lower left part and the right part of FIG. 13, the marker depicted in the second image is transferred to the three-dimensional vascular central line image, and the marker position in the three-dimensional vascular central line image is detected. The detection position of the marker in the three-dimensional vascular central line image is estimated to be the treatment position, and the circumferential orbit is calculated around the estimated treatment position similarly to the first embodiment.

In the flowchart of FIG. 12, the processing of the steps ST33 and ST34 corresponds to the above-described function of the third embodiment. The processing of the steps ST30, ST31, ST32, ST35, and ST36 is the same as that of the first embodiment, According to the X-ray diagnostic apparatus 1 of the third embodiment, the treatment position in the three-dimensional vascular central line image can be readily detected by detecting the marker provided in the intravascular device.

FOURTH EMBODIMENT

Figure 14:
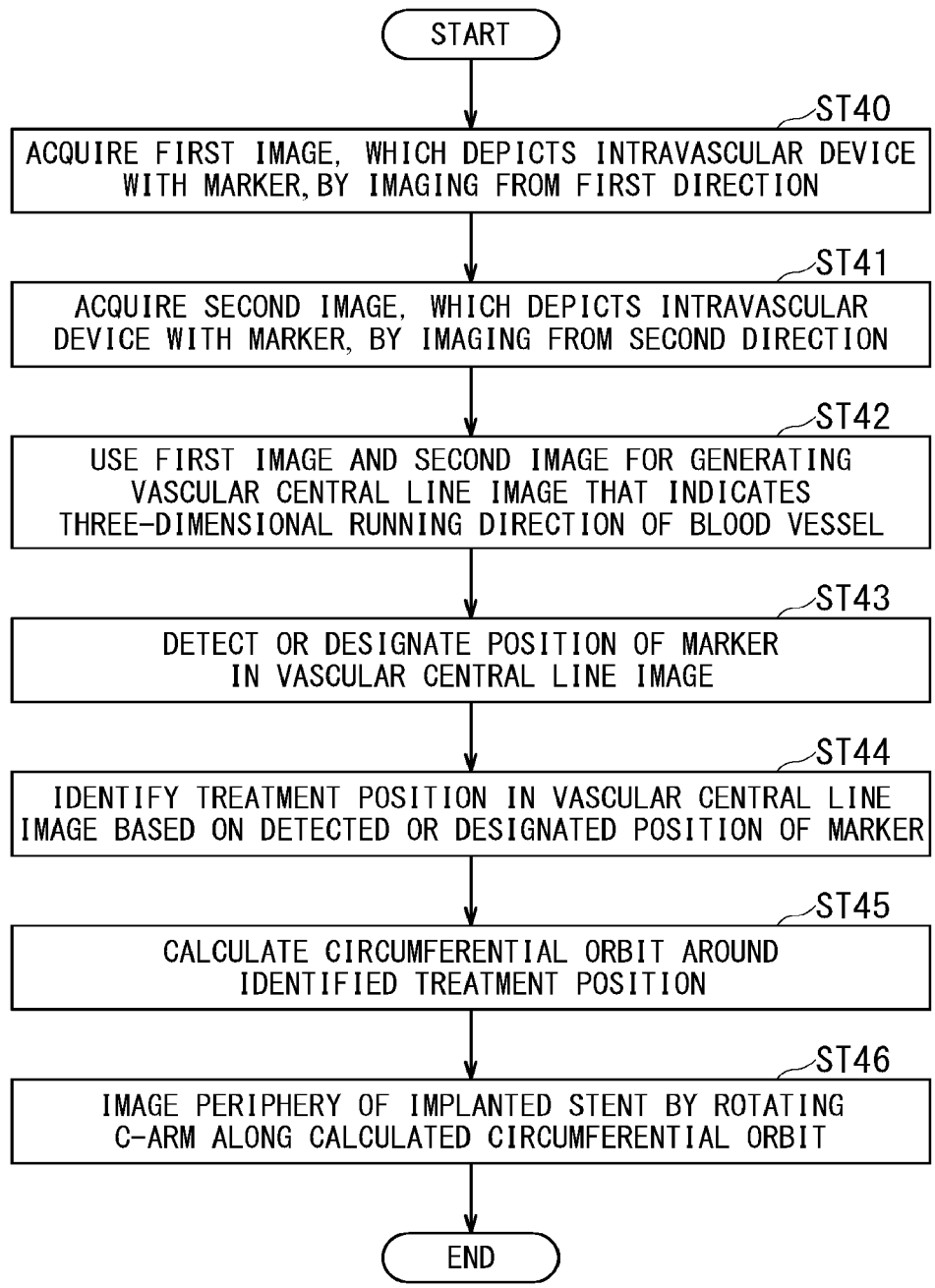
FIG. 14 is a flowchart illustrating an operation to be executed by the X-ray diagnostic apparatus of each of the fourth and fifth embodiments.
Figure 15:
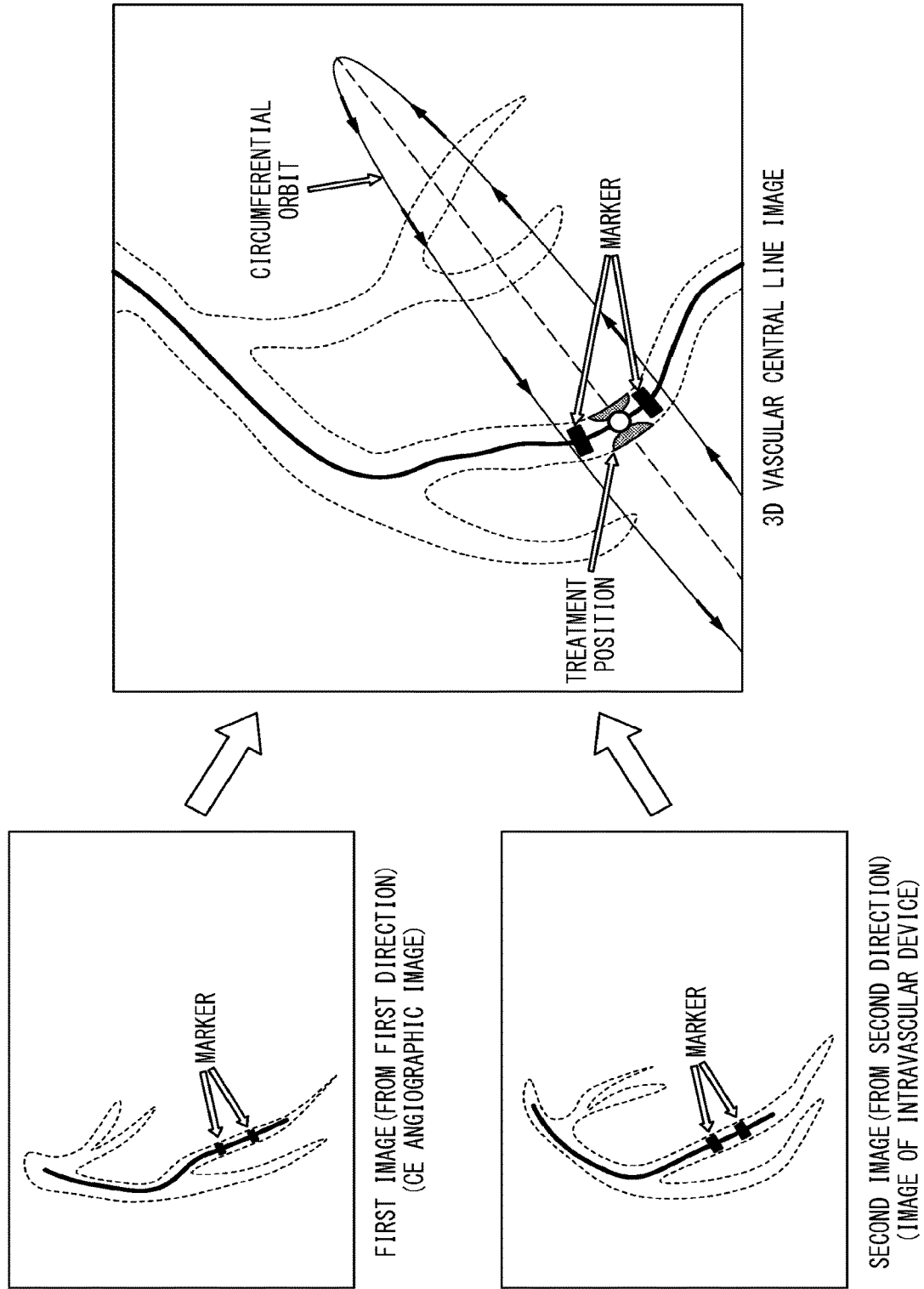
FIG. 15 is a schematic diagram illustrating an operation concept of the X-ray diagnostic apparatus of each of the fourth and fifth embodiments.

FIG. 14 is a flowchart illustrating an operation to be executed by the X-ray diagnostic apparatus 1 of the fourth embodiment. FIG. 15 is a schematic diagram illustrating an operation concept of the X-ray diagnostic apparatus of the fourth embodiment.

In the X-ray diagnostic apparatus 1 of the above-described third embodiment, a Contrast Enhanced angiographic image acquired by using a contrast agent is used as the first image similarly to the first and second embodiments, and the second image is acquired by using an intravascular device with a marker, without using the contrast agent. By contrast, in the X-ray diagnostic apparatus 1 of the fourth embodiment as shown in the upper left part and lower left part of FIG. 15, for each of the first image and the second image, an angiographic image, in which the intravascular device with a marker is depicted without using the contrast agent, is used. In each of the first image and the second image, a guidewire indicated by the thick solid line is depicted in addition to the marker.

The first image and the second image are images obtained by imaging the intravascular device with a marker inserted into the coronary artery of the treatment target from two different directions under the state where movement of the marker is stopped for a predetermined time or more. On the basis of these first image and second images depicting the intravascular device with a marker, a three-dimensional vascular central line image in which the marker is depicted is generated as shown in the right part of FIG. 15.

In the flowchart shown in FIG. 14, the processing of the step ST40 is different from that of the third embodiment, and the processing of all the other steps ST41 to ST46 is substantially the same as the processing of the steps ST31 to 36 of the third embodiment.

The position where movement of the marker has stopped for a predetermined time or more can be considered as the position where the stent is placed or to be placed, similarly to the third embodiment. Thus, the X-ray diagnostic apparatus 1 of the fourth embodiment can readily detect the treatment position in the three-dimensional vascular central image by detecting the marker position in the three-dimensional vascular central line image similarly to the third embodiment.

FIFTH EMBODIMENT

In the above-described fourth embodiment, the treatment-position reception/detection function 130 of the apparatus automatically detects the treatment position by detecting the marker position from the three-dimensional vascular central line image. In the fifth embodiment, a user refers to the three-dimensional vascular central line image on which the marker is depicted, and the user manually designates the treatment position.

Specifically, in the step ST43 in FIG. 14, the user designates the marker position for the three-dimensional vascular central line image displayed on the display 13. In the subsequent step ST44, the treatment position in the three-dimensional vascular central line image is specified on the basis of the designated marker position.

According to the X-ray diagnostic apparatus 1 of the fifth embodiment, though the manual operation by the user is included in part, the same effect as that of the fourth embodiment can be obtained.

SIXTH EMBODIMENT

Figure 16:
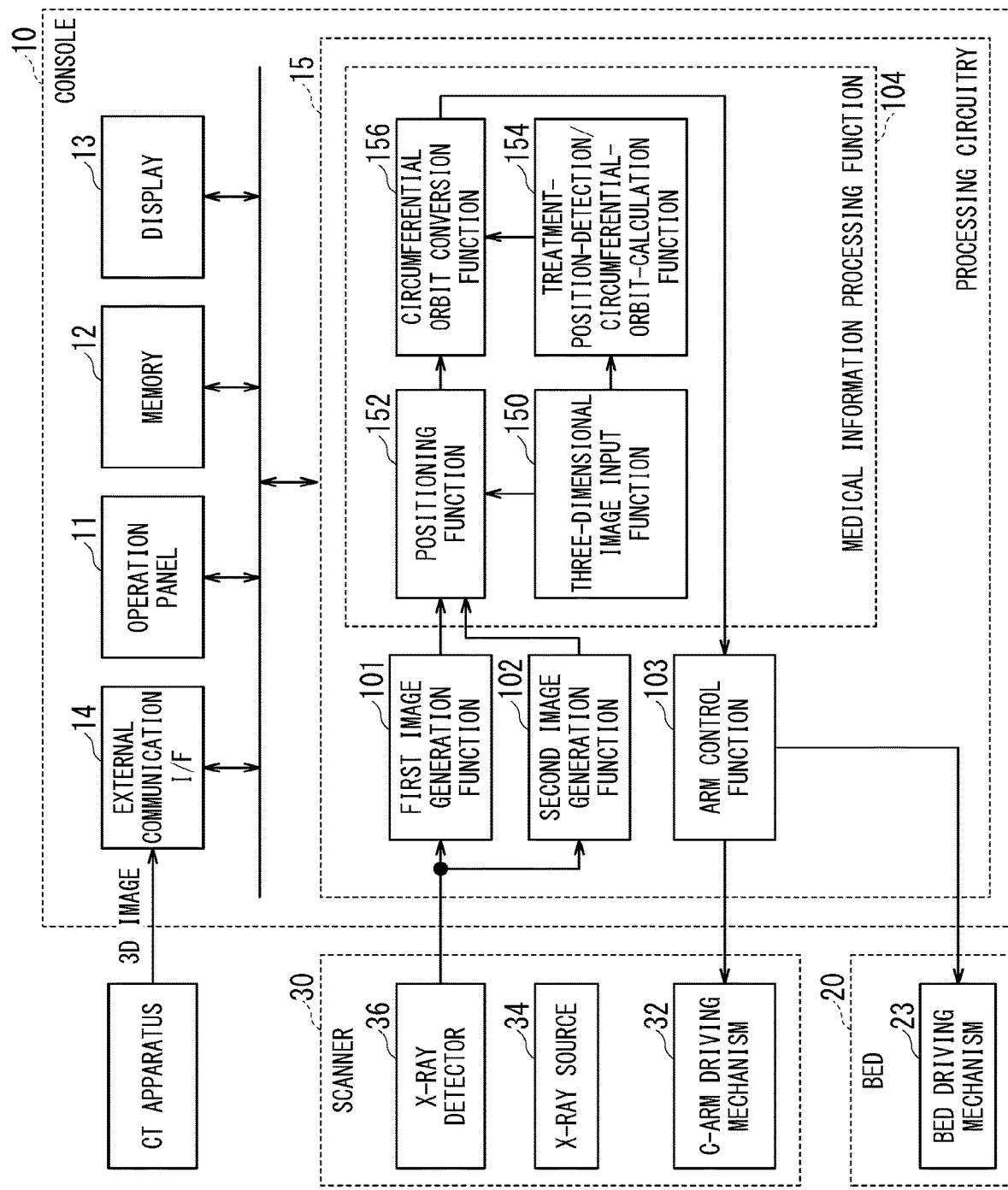
FIG. 16 is a block diagram illustrating a configuration and functions of the console according to the sixth embodiment.
Figure 17:
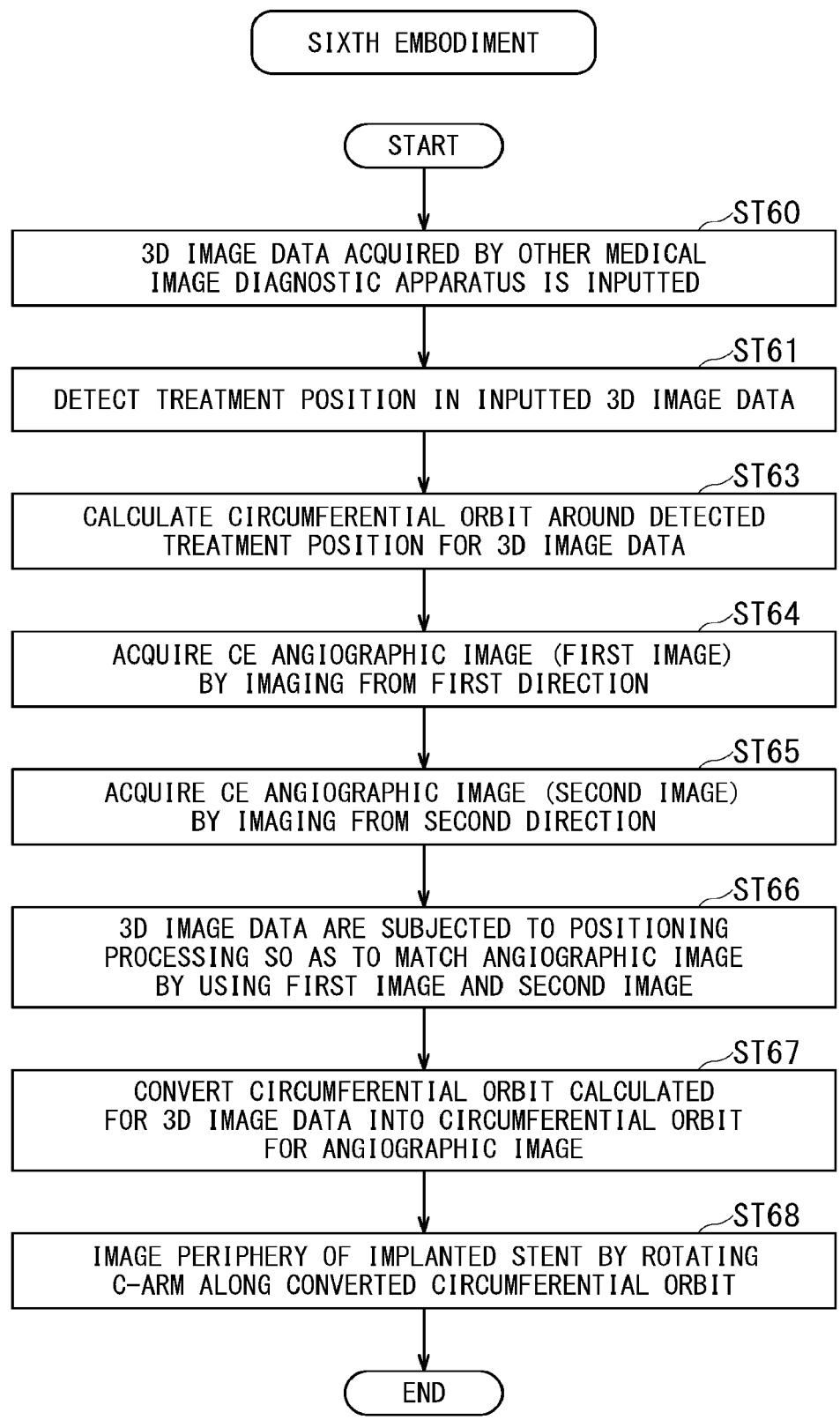
FIG. 17 is a flowchart illustrating an operation to be executed by the X-ray diagnostic apparatus according to the sixth embodiment.
Figure 18:
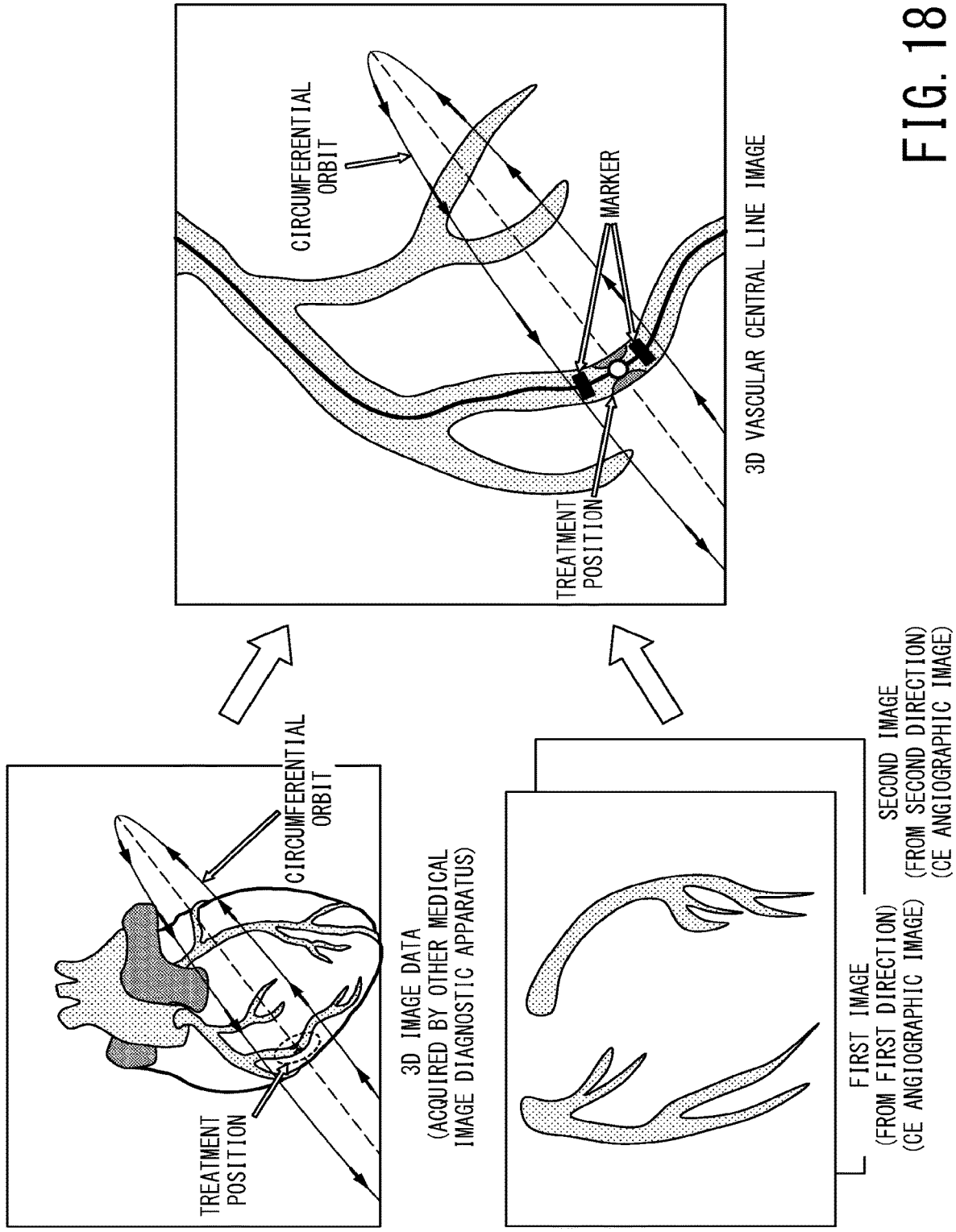
FIG. 18 is a schematic diagram illustrating an operation concept of the X-ray diagnostic apparatus according to the sixth embodiment.

FIG. 16 is a block diagram illustrating a detailed configuration and functions of the X-ray diagnostic apparatus 1 according to the sixth embodiment. FIG. 17 is a flowchart illustrating an operation to be executed by the X-ray diagnostic apparatus 1 according to the sixth embodiment. FIG. 18 is a schematic diagram illustrating an operation concept of the X-ray diagnostic apparatus 1 according to the sixth embodiment.

In the first to fifth embodiments described so far, the circumferential orbit is calculated for the treatment position of the three-dimensional vascular central line image generated from a plurality of images that are imaged by the X-ray diagnostic apparatus 1. In the X-ray diagnostic apparatus 1 of the sixth embodiment, the circumferential orbit is calculated for the treatment position of a three-dimensional image acquired by a medical image diagnostic apparatus other than the X-ray diagnostic apparatus 1, for example, a CT apparatus.

Hereinafter, the operation of the sixth embodiment will be described according to the step numbers in the flowchart of FIG. 17.

First, in the step ST60, three-dimensional image data of the patient acquired by one of other medical image diagnostic apparatuses, for example, a CT apparatus, are inputted. The three-dimensional image data are inputted from, for example, a CT apparatus or an image server via the external communication I/F 14 by the three-dimensional image input function 150 in FIG. 16.

In the next step ST61, the treatment position in the inputted three-dimensional image data is detected. The treatment position may be automatically detected by the apparatus (X-ray diagnostic apparatus 1). Additionally or alternatively, the X-ray diagnostic apparatus 1 may cause the display 13 to display the inputted three-dimensional image so as to receive the treatment position to be specified by the user and then detect the treatment position.

In the next step ST63, the circumferential orbit around the detected treatment position is calculated for the three-dimensional image data. Specifically, on the basis of the detected treatment position and the running direction of the blood vessel corresponding to the treatment position, the circumferential orbit around the treatment position is calculated in a plane that is orthogonal to the running direction of the blood vessel and includes the treatment position. The processing of the steps ST61 and ST63 is executed by the treatment-position-detection/circumferential-orbit-calculation function 154 in FIG. 16. The processing of steps ST61 and ST63 is performed before the stent treatment, for example, at the planning stage of the stent treatment.

The upper left part of FIG. 18 illustrates the three-dimensional image data of the patient acquired by one of other medical image diagnostic apparatuses. In this figure, the treatment position detected for the three-dimensional image data, and the circumferential orbit calculated around the detected treatment position are further depicted.

The processing from the step ST64 is performed at the stage of the stent treatment.

First, in the step ST64, this apparatus (X-ray diagnostic apparatus 1) is used for acquiring a CE angiographic image obtained by injecting a contrast agent into the object from the first direction, and the acquired image is treated as the first image.

Similarly, in the step ST65, a CE angiographic image imaged from the second direction is acquired as the second image. The processing of the steps ST64 and ST65 is performed by the first image generation function 101 and the second image generation function 102 in FIG. 16. The lower left part of FIG. 18 illustrates the two angiographic images acquired as the first image and the second image.

In the next step ST66, the three-dimensional image data acquired by the other medical image diagnostic apparatus are subjected to positioning processing (or alignment processing) so as to positionally match the angiographic images acquired in the steps ST64 and ST65, by using, for example, correlation processing. This positioning processing is performed by the positioning function 152 shown in FIG. 16. Any one of the CE angiographic image of the first image and the second image may be used for performing the positioning processing on the three-dimensional image data acquired by the other medical image diagnostic apparatus, i.e., the three-dimensional image data may be subjected to positioning processing so as to positionally match any one of the first image and the second image. The right part of FIG. 18 illustrates a three-dimensional image that has been subjected to the positioning processing so as to positionally match the angiographic image.

In the next step ST67, the positioning data, such as coordinate conversion data calculated by the positioning processing, are used for converting the circumferential orbit calculated for the three-dimensional image data into the circumferential orbit for the angiographic image. The processing of the step ST67 is performed by the circumferential orbit conversion function 156 shown in FIG. 16.

The processing of the step ST68 is substantially the same as that of the first to fifth embodiments, and the C-arm 33 is rotated along the converted circumferential orbit such that the periphery of the position of the implanted stent is imaged.

Since the X-ray diagnostic apparatus 1 of the sixth embodiment can calculate the circumferential orbit at the planning stage of the stent treatment by using the three-dimensional image data that are acquired by imaging the patient with the use of the other medical diagnostic imaging apparatus, the time for performing the stent treatment can be shortened.

OTHER EMBODIMENTS

In the first to sixth embodiments, the X-ray diagnostic apparatus 1 achieves all the functions from processing the generated or acquired image to calculating the circumferential orbit and performing imaging while controlling the C-arm on the basis of the calculated circumferential orbit. The embodiments of the present invention are not limited to the above-described aspect, and one or more of the above-described functions may be performed by an apparatus other than the X-ray diagnostic apparatus 1, for example, by a medical information processing apparatus 300. In detail, the image generated by the X-ray diagnostic apparatus 1 may be inputted to the medical information processing apparatus 300 that calculates the circumferential orbit by using the inputted image.

Figure 19:
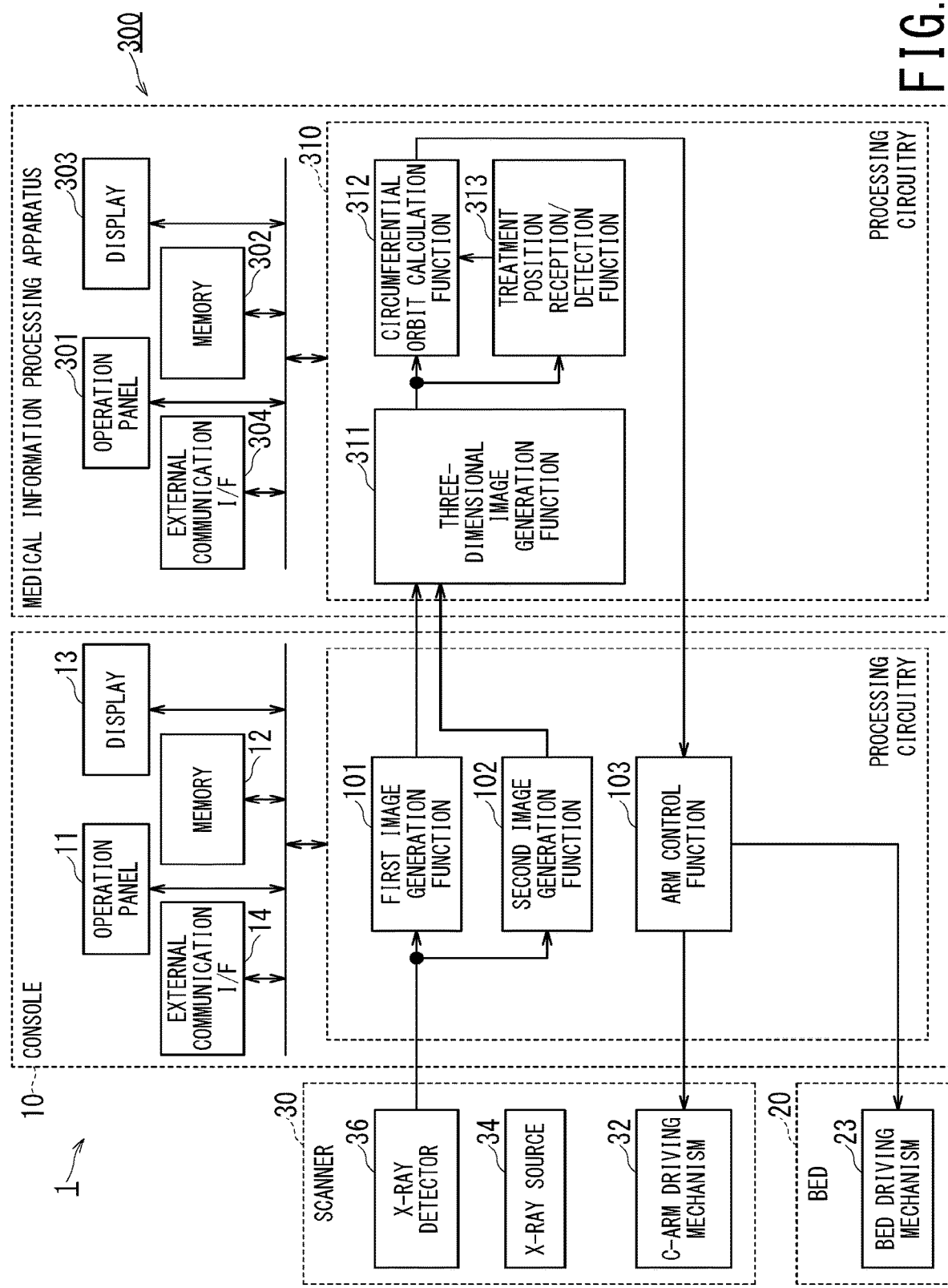
FIG. 19 is a configuration diagram illustrating a first configuration of a medical information processing apparatus among other embodiments.
Figure 20:
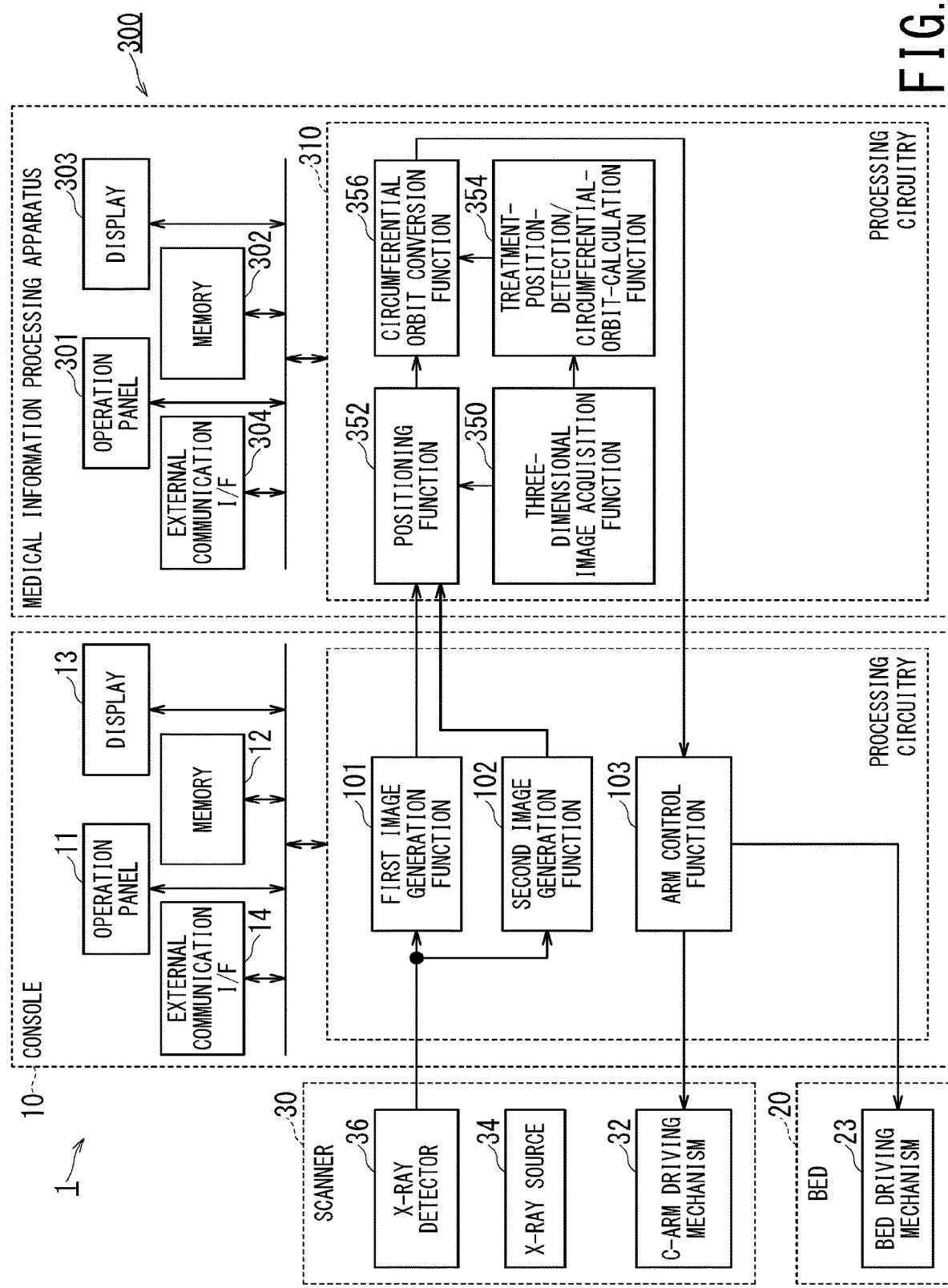
FIG. 20 is a configuration diagram illustrating a second configuration of a medical information processing apparatus among other embodiments.

FIG. 19 and FIG. 20 are block diagrams illustrating the respective configurations of the medical information processing apparatus 300 having such functions and the X-ray diagnostic apparatus 1 from which such functions are omitted.

FIG. 19 mainly illustrates a configuration of the medical information processing apparatus 300 that implements the function corresponding to the medical information processing function 104 in the block diagram (FIG. 2 or FIG. 9) corresponding to the first to fifth embodiments.

The medical information processing apparatus 300 is a computer such as a workstation, and includes an operation panel 301, a memory 302, a display 303, an external communication I/F 304, and processing circuitry 310. The processing circuitry 310 implements each of the three-dimensional image generation function 311, the circumferential orbit calculation function 312, and the treatment position reception/detection function 313.

Since each configuration and each function in the above-described FIG. 19 have already been described as a configuration and function with the same name in the first to fifth embodiments, duplicate description is omitted.

FIG. 20 illustrates a configuration of the medical information processing apparatus 300 that implements the function corresponding to the medical information processing function 104 in the block diagram of FIG. 16 in the sixth embodiment. The medical information processing apparatus 300 shown in FIG. 20 is also a computer such as a workstation and includes the operation panel 301, the memory 302, the display 303, the external communication I/F 304, and the processing circuitry 310 that implements each of the three-dimensional image acquisition function 350, the positioning function 352, and the treatment-position-detection/circumferential-orbit-calculation function 354. Since each configuration and each function in the above-described FIG. 20 have already been described as a configuration and function with the same name in the sixth embodiment, duplicate description is omitted.

As described above, the X-ray diagnostic apparatus 1 of each embodiment can readily and reliably check a treatment result of PCI such as the state of the implanted stent.

The treatment position in the description of each embodiment includes not only the site where the stent has been implanted but also the site where the stent is to be placed, and further includes: a stenosis site of a blood vessel that is a target for determining whether or not to place a stent; and a diagnosis target site where stenosis of a blood vessel may have been caused. "The treatment position" in the description of each embodiment is one of examples of "target position" recited in the claims. For example, in order to check the degree of stenosis, fluoroscopic imaging may be performed by using a contrast agent and rotating the C-arm may on the orbit around the stenosis site. In such a case, the stenosis site is included in the "target position". As a result of checking the degree of stenosis, there are a case where treatment such as stent placement is performed and a case where treatment is not performed.

In each of the above-described embodiments, a description has been given of the case where the orbit around the target position (or the treatment position) in the blood vessel is calculated on the basis of the running direction of the blood vessel and the X-ray source and the X-ray detector are rotated by the arm to image the periphery of the target position along the calculated orbit. However, when the arm is rotated along the calculated orbit, there is a possibility that the X-ray source, the X-ray detector, or part of the arm may cause mechanical interference with surrounding components and/or instruments. In such a case, it is preferred to newly determine another orbit closest to the calculated orbit within a range where the mechanical interference does not occur and to rotate the X-ray source and the X-ray detector by the arm on the basis of the newly determined orbit.

In the above-described embodiment, a description has been given of the case where the orbit around the target position in the blood vessel is calculated and the periphery of the target position is imaged along the calculated orbit. However, in some cases, it is not necessarily required to continuously rotate the arm along the orbit at the time of imaging the periphery of the target position. For example, there is a case where it is sufficient to image the target position of the blood vessel from a plurality of directions. In such a case, it is sufficient that the positions of the X-ray source and the X-ray detector are controlled by using the arm such that the target position of the blood vessel is imaged from at least two different directions to be determined depending on the running direction of the blood vessel. In this case, for example, the positions of the X-ray source and the X-ray detector are controlled by using the arm such that the target position is imaged from at least two different directions within a plane orthogonal to the running direction of the blood vessel and including the target position.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. an X-ray diagnostic apparatus, comprising:
   an X-ray source;
   an X-ray detector;
   an arm configured to support the X-ray source and the X-ray detector; and
   processing circuitry configured to
      identify a three-dimensional running direction of blood flow of a blood vessel of an object from a plurality of images that are obtained by using the X-ray source and the X-ray detector to image the object from at least two different directions, and
      calculate an orbit around a target position of the blood vessel based on the three-dimensional running direction of the blood flow, and
      rotate the X-ray source and the X-ray detector by using the arm in such a manner that a periphery of the target position is imaged along the calculated orbit.

2. The X-ray diagnostic apparatus according to claim 1, wherein the processing circuitry is further configured to control positions of the X-ray source and the X-ray detector by using the arm in such a manner that the target position is imaged from the at least two different directions within a plane orthogonal to the three-dimensional running direction, the plane including the target position.

3. The X-ray diagnostic apparatus according to claim 1, wherein the processing circuitry is further configured to calculate the orbit within a plane that is orthogonal to the three-dimensional running direction and includes the target position.

4. The X-ray diagnostic apparatus according to claim 1, wherein the processing circuitry is further configured to rotate the X-ray source and the X-ray detector so that the target position, which is a position where a stent is placed, is imaged.

5. The X-ray diagnostic apparatus according to claim 1, wherein the processing circuitry is further configured to identify the three-dimensional running direction from a first image and a second image, the first image being obtained by injecting a contrast agent into the blood vessel and imaging the blood vessel, and the second image being obtained by inserting a device attached to a catheter into the blood vessel and imaging the blood vessel from a direction different from an imaging direction of the first image.

6. The X-ray diagnostic apparatus according to claim 1, wherein the processing circuitry is further configured to
divide a predetermined range along the three-dimensional running direction into a plurality of regions,
calculate respective preliminary orbits for the plurality of regions, and
select the orbit from the preliminary orbits depending on a designation by a user.

7. The X-ray diagnostic apparatus according to claim 5, wherein:
the device is an intravascular ultrasound imaging device; and
the processing circuitry is further configured to
estimate the target position based on an association between stenosis information obtained from an image imaged by the intravascular ultrasound imaging device and a position of the intravascular ultrasound imaging device depicted in the second image, and
calculate the orbit based on an estimated target position.

8. The X-ray diagnostic apparatus according to claim 5, wherein:
the second image is an image in which at least one marker provided in at least one of a tip of the catheter and a location near the device is further depicted; and
the processing circuitry is further configured to estimate the target position based on a position of the at least one marker depicted in the second images, and calculate the orbit based on an estimated target position.

9. The X-ray diagnostic apparatus according to claim 1, wherein the processing circuitry is further configured to identify the three-dimensional running direction from a first image and a second image, the first image being obtained by imaging a device inserted into the blood vessel, the device being attached to a catheter, and the second image being obtained by imaging the device from a direction different from an imaging direction of the first image.

10. The X-ray diagnostic apparatus according to claim 1, wherein the processing circuitry is further configured to identify the three-dimensional running direction from a first image and a second image, the first image being obtained by imaging a device inserted into the blood vessel, the device being attached to a catheter, and the second image being obtained by imaging the device from a direction different from an imaging direction of the first image.

11. The X-ray diagnostic apparatus according to claim 10, wherein:
each of the first image and the second image is an image in which at least one marker provided in at least one of a tip of the catheter and a location near the device is depicted; and
the processing circuitry is further configured to
estimate the target position based on each position of the at least one marker depicted in the first image and the second image, and
calculate the orbit based on an estimated target position.

12. The X-ray diagnostic apparatus according to claim 10, wherein:
each of the first image and the second image is an image in which at least one marker provided in at least one of a tip of the catheter and a location near the device is depicted; and
the processing circuitry is further configured to
cause a display to display the first image and the second image in such a manner that designation of the target position can be received from a user in association with display of the first image and the second image, and
calculate the orbit based on the target position designated by the user.

13. The X-ray diagnostic apparatus according to claim 1, wherein the processing circuitry is further configured to
determine whether or not mechanical interference occurs in a case of rotating the arm along the calculated orbit,
determine a new orbit closest to the calculated orbit within a range when the mechanical interference does not occur, when it is determined that the mechanical interference occurs in a case of rotating the arm along the calculated orbit, and
rotate the X-ray source and the X-ray detector by using the arm based on the new orbit.

14. An X-ray diagnostic apparatus, comprising:
an X-ray source;
an X-ray detector;
an arm configured to support the X-ray source and the X-ray detector; and
processing circuitry configured to
acquire a three-dimensional image generated by imaging an object,
receive a designation of a target position of a blood vessel of the object in the three-dimensional image,
calculate an original orbit around the target position based on a location of the target position and a running direction of blood flow of the blood vessel corresponding to the target position in such a manner that the original orbit is within a plane orthogonal to the running direction of the blood vessel and including the target position,
perform positioning processing on the three-dimensional image in such a manner that the three-dimensional image positionally matches an X-ray image obtained by using the X-ray source and the X-ray detector to image the object,
convert the original orbit calculated for the three-dimensional image into a converted orbit for the X-ray source and the X-ray detector, and cause the arm to rotate the X-ray source and the X-ray detector along the converted orbit in such a manner that a periphery of the target position is imaged.

15. A medical image processing apparatus, comprising: processing circuitry configured to
    acquire a plurality of images that are obtained by using an X-ray source and an X-ray detector for imaging an object from at least two different angles, the X-ray source and the X-ray detector being supported by an arm,
    identify a three-dimensional running direction of blood flow of a blood vessel of the object from the plurality of images,
    calculate a first orbit around a target position in the blood vessel in such a manner that the first orbit is within a plane orthogonal to the three-dimensional running direction of the blood flow and including the target position, and
    output control data for causing the arm to rotate the X-ray source and the X-ray detector in such a manner that a periphery of the target position is imaged along the first orbit.

16. The medical image processing apparatus according to claim 15, wherein the processing circuitry is further configured to
    acquire a three-dimensional image generated by imaging the object,
    receive a designation of the target region in the three-dimensional image,
    calculate a second orbit around the target position in the three-dimensional image based on the target position and a running direction of the blood flow corresponding to the target position in the three-dimensional image in such a manner that the second orbit is within a plane orthogonal to the running direction of the blood flow and including the target position,
    perform positioning processing on the three-dimensional image in such a manner that the three-dimensional image positionally matches an X-ray image obtained by using the X-ray source and the X-ray detector to image the object,
    convert the second orbit calculated for the three-dimensional image into a third orbit for the X-ray source and the X-ray detector, and
    output control data for causing the arm to rotate the X-ray source and the X-ray detector in such a manner that a periphery of the target position is imaged along the third orbit.

* * * * *